US010112914B2

(12) United States Patent
Muthukaman et al.

(10) Patent No.: US 10,112,914 B2
(45) Date of Patent: Oct. 30, 2018

(54) POLYMORPHS OF A MPGES-1 INHIBITING TRIAZOLONE COMPOUND

(71) Applicant: Glenmark Pharmaceuticals S.A., La Chaux-de-Fonds (CH)

(72) Inventors: Nagarajan Muthukaman, Tamil Nadu (IN); Laxmikant A. Gharat, Maharashtra (IN); Suresh M. Kadam, Maharashtra (IN); Sachin Gavhane, Maharashtra (IN); Sandeep B. Khandagale, Maharashtra (IN); Sunil P. Nirgude, Maharashtra (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days.

(21) Appl. No.: 15/573,387

(22) PCT Filed: Jun. 13, 2016

(86) PCT No.: PCT/IB2016/053467
§ 371 (c)(1),
(2) Date: Nov. 10, 2017

(87) PCT Pub. No.: WO2016/199104
PCT Pub. Date: Dec. 15, 2016

(65) Prior Publication Data
US 2018/0134671 A1  May 17, 2018

(30) Foreign Application Priority Data
Jun. 12, 2015 (IN) .......................... 2275/MUM/2015

(51) Int. Cl.
*C07D 249/12* (2006.01)
*A61P 29/00* (2006.01)
(Continued)

(52) U.S. Cl.
CPC ............ *C07D 249/12* (2013.01); *A61P 29/00* (2018.01); *G01N 23/20075* (2013.01); *G01N 2021/3595* (2013.01)

(58) Field of Classification Search
None
See application file for complete search history.

(56) References Cited

FOREIGN PATENT DOCUMENTS

| WO | WO-2012087771 A1 | 6/2012 | |
| WO | WO 2013/186692 | * 12/2013 | ........... C07D 403/12 |
| WO | WO-2013186692 A1 | 12/2013 | |

OTHER PUBLICATIONS

Caira, et al., Crystalline Polymorphism of Organic Compounds, Topics in Current Chemistry, 1998, 198:163-208.
(Continued)

*Primary Examiner* — Alicia L Otton
(74) *Attorney, Agent, or Firm* — Blank Rome LLP

(57) ABSTRACT

The present application relates to solid state forms of a triazolone compound which exhibit mPGES-1 enzyme inhibition activity, specifically N-(4-chloro-3-(5-oxo-1-(4-(trifluoromethyl)phenyl)-4,5-dihydro-1H-1,2,4-triazol-3-yl) benzyl) pivalamide (Compound of formula II), and process for preparation thereof.

(Continued)

XRPD Pattern of Form I

(51) Int. Cl.
 *G01N 23/20* (2018.01)
 *G01N 21/35* (2014.01)

(56) References Cited

OTHER PUBLICATIONS

Hilfiker, et al.. Polymorphism in the Pharmaceutical Industry, 2006, pp. 1-9.
Yu, et al., Amorphous Pharmaceutical Solids: Preparation, Characterization and Stabilization, Advanced Drug Delivery Reviews, 2001, 48:1:27-42.
International Search Report issued in PCT/IB2016/053467 dated Nov. 14, 2016.

\* cited by examiner

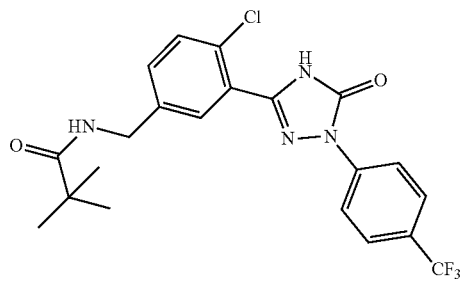

(II)

10 Claims, 4 Drawing Sheets

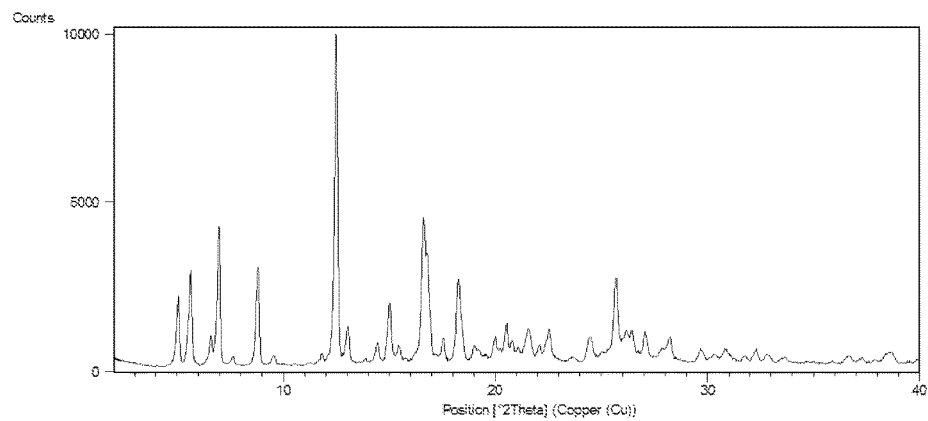
Fig.1: XRPD Pattern of Form I
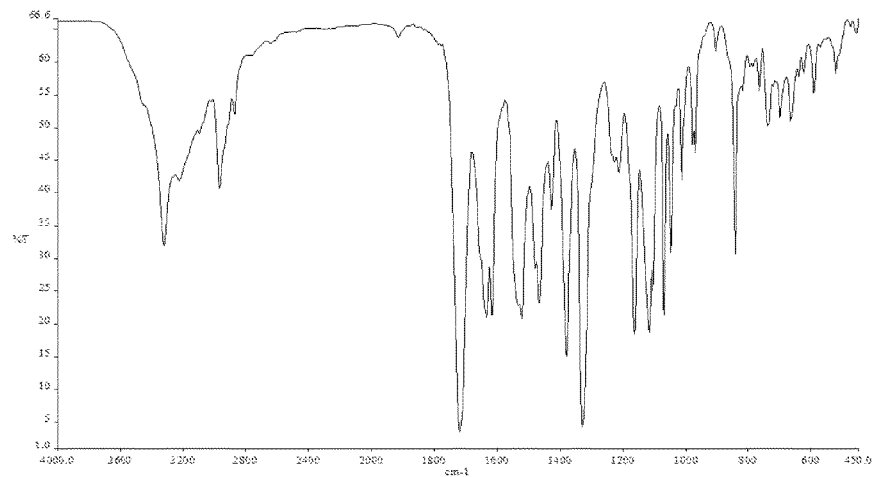
Fig 2: IR Spectrum of Form I

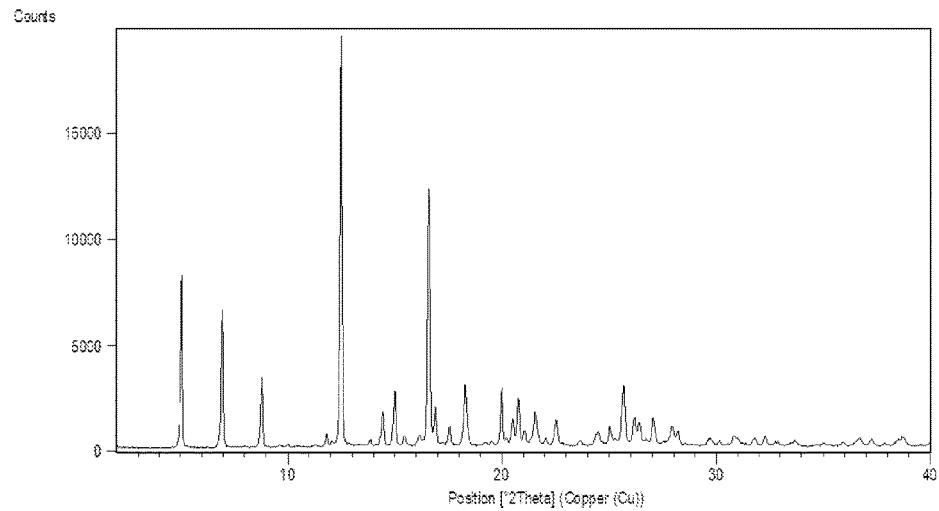
Fig.3: XRPD Pattern of Form II
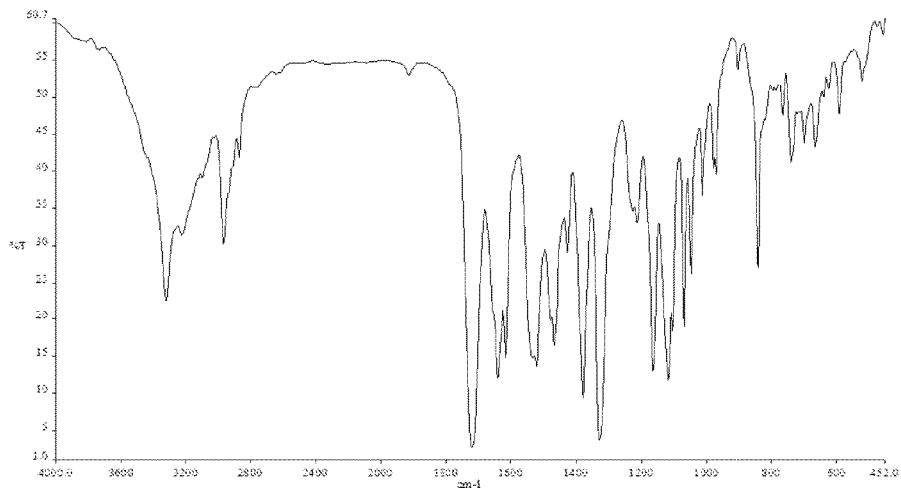
Fig 4: IR Spectrum of Form II

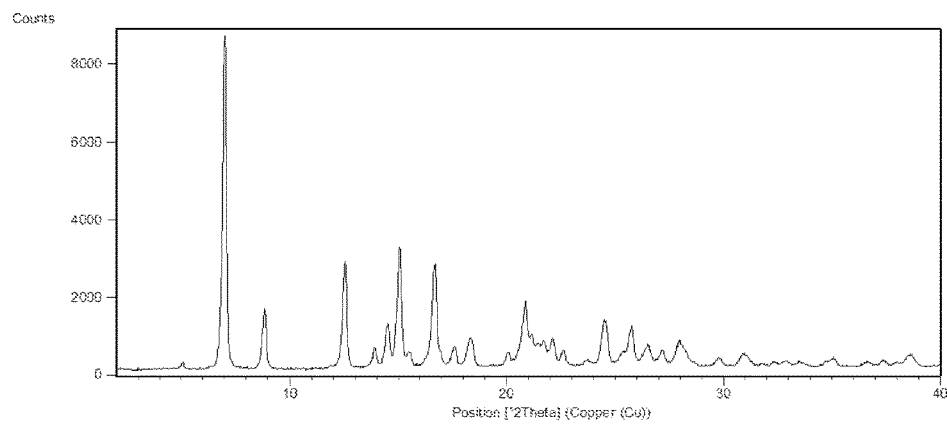
Fig.5: XRPD Pattern of Form III
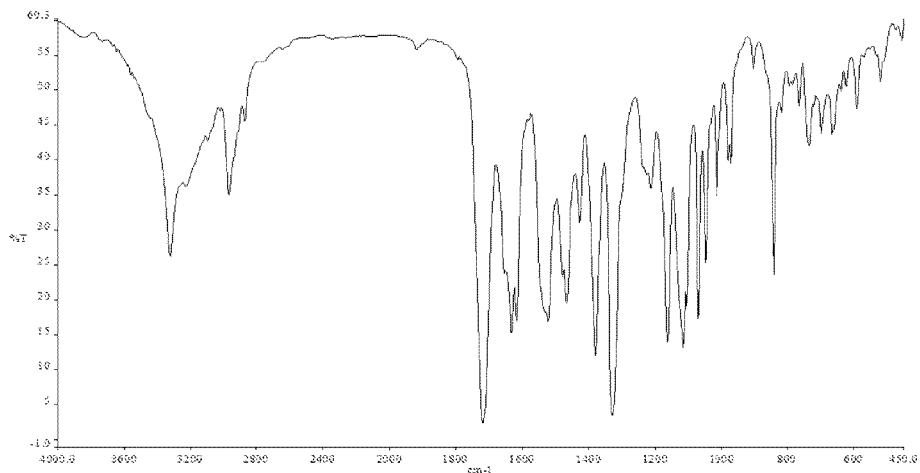
Fig 6: IR Spectrum of Form III

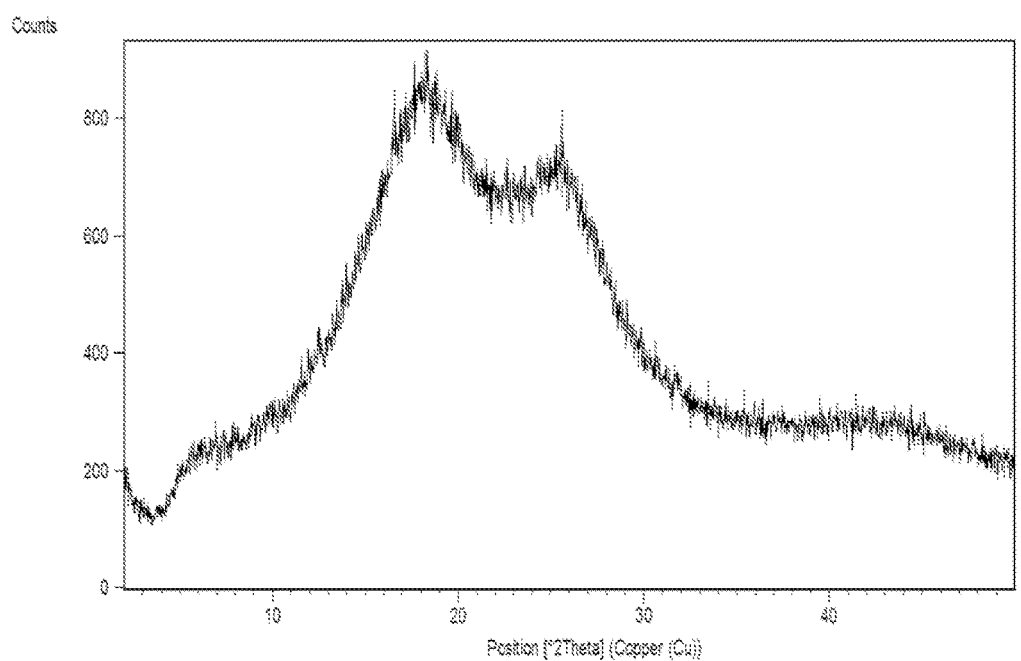
Fig.7: XRPD Pattern of Amorphous Form

POLYMORPHS OF A MPGES-1 INHIBITING TRIAZOLONE COMPOUND

RELATED APPLICATIONS

This application is a national stage of International Patent Application No. PCT/IB2016/053467, filed on Jun. 13, 2016, which claims the benefit of Indian Provisional Application No. 2275/MUM/2015, filed on Jun. 12, 2015, which is hereby incorporated by reference in its entirety.

TECHNICAL FILED OF THE INVENTION

The present application relates to solid state forms of a triazolone compound which exhibit mPGES-1 enzyme inhibition activity, specifically N-(4-chloro-3-(5-oxo-1-(4-(trifluoromethyl)phenyl)-4,5-dihydro-1H-1,2,4-triazol-3-yl)benzyl) pivalamide, and process for preparation thereof.

BACKGROUND OF THE INVENTION

There are many diseases or disorders that are inflammatory in their nature. One of the major problems associated with existing treatments of inflammatory conditions is inadequate efficacy and/or the prevalence of side effects. Inflammatory diseases that affect the population include asthma, inflammatory bowel disease, rheumatoid arthritis, osteoarthritis, rhinitis, conjunctivitis and dermatitis. Inflammation is also a common cause of pain.

The enzyme cyclooxygenase (COX) converts arachidonic acid to an unstable intermediate, prostaglandin $H_2$ ($PGH_2$), which is further converted to other prostaglandins, including $PGE_2$, $PGF_{2\alpha}$, $PGD_2$, prostacyclin and thromboxane $A_2$. These arachidonic acid metabolites are known to have pronounced physiological and pathophysiological activity, including pro-inflammatory effects. The COX enzyme exists in two forms, one that is constitutively expressed in many cells and tissues (COX-1), and another that in mast cells and tissues is induced by pro-inflammatory stimuli, such as cytokines, during an inflammatory response (COX-2).

Among all prostaglandin metabolites, $PGE_2$ is particularly known to be a strong pro-inflammatory mediator, and is also known to induce fever and pain. Consequently, numerous drugs have been developed with a view to inhibiting the formation of $PGE_2$, including "NSAIDs" (non-steroidal anti-inflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage of reducing the formation of all metabolites of $PGH_2$, thereby decreasing the beneficial properties of some of the metabolites. In view of this, drugs which act by inhibition of COXs are suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

A combination of pharmacological, genetic and neutralizing antibody approaches demonstrates the importance of $PGE_2$ in inflammation. The conversion of $PGH_2$ to $PGE_2$ by prostaglandin E synthases (PGES) may, therefore, represent a pivotal step in the propagation of inflammatory stimuli. There are two microsomal prostaglandin E synthases (mPGES-1 and mPGES-2), and one cytosolic prostaglandin E synthase (cPGES). mPGES-1 is an inducible PGES after exposure to pro-inflammatory stimuli. mPGES-1 is induced in the periphery and CNS by inflammation, and represents therefore a target for acute and chronic inflammatory disorders. $PGE_2$ is a major prostanoid, produced from arachidonic acid liberated by phospholipases (PLAs), which drives the inflammatory processes. Arachidonic acid is transformed by the action of prostaglandin H synthase (PGH synthase, cycloxygenase) into $PGH_2$ which is a substrate for mPGES-1, the terminal enzyme transforming $PGH_2$ to the pro-inflammatory $PGE_2$.

Agents that are capable of inhibiting the action of mPGES-1, and thus reducing the formation of the specific arachidonic acid metabolite $PGE_2$, are beneficial in the treatment of inflammation. Further, agents that are capable of inhibiting the action of the proteins involved in the synthesis of the leukotrienes are also beneficial in the treatment of asthma and COPD.

Blocking the formation of $PGE_2$ in animal models of inflammatory pain results in reduced inflammation, pain and fever response (Kojima et. al, *The Journal of Immunology* 2008, 180, 8361-6; Xu et. al., *The Journal of Pharmacology and Experimental Therapeutics* 2008, 326, 754-63). In abdominal aortic aneurism, inflammation leads to connective tissue degradation and smooth muscle apoptosis ultimately leading to arotic dilation and rupture. In animals lacking mPGES-1 a slower disease progression and disease severity has been demonstrated (Wang et. al., *Circulation*, 2008, 117, 1302-1309).

Several lines of evidence indicate that $PGE_2$ is involved in malignant growth. $PGE_2$ facilitates tumor progression by stimulation of cellular proliferation and angiogenesis and by modulation of immunosupression. In support of a role for $PGE_2$ in cancers, genetic deletion of mPGES-1 in mice suppresses intestinal tumourogenesis (Nakanishi et. al., *Cancer Research* 2008, 68(9), 3251-9). In human beings, mPGES-1 is also upregulated in cancers such as colorectal cancer (Schroder, *Journal of Lipid Research* 2006, 47, 1071-80).

International Publication Number WO 2013/186692 discloses triazolone compounds of formula (I) (disclosed as formula (III) in the specification of WO 2013/186692)

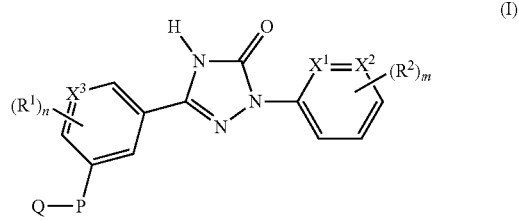

wherein, $X^1$, $X^2$ and $X^3$ are each independently selected from CH and N;

P is selected from —$CH_2NHC(O)$— and —$CH_2NHS(O)_2$—;

Q is selected from $C_{1-8}$alkyl, halo$C_{1-8}$alkyl, $C_{1-8}$alkoxy$C_{1-8}$alkyl, hydroxy$C_{1-8}$alkyl, carboxyl$C_{1-8}$alkyl, $C_{3-12}$cycloalkyl, $C_{6-14}$aryl, 3-15 membered heterocyclyl, and 5-14 membered heteroaryl;

each occurrence of $R^1$ is independently selected from halogen, cyano, $C_{1-8}$alkyl, $C_{1-8}$alkoxy, halo$C_{1-8}$alkyl and $C_{3-6}$cycloalkyl;

each occurrence of $R^2$ is independently selected from halogen, cyano, $C_{1-8}$alkyl, $C_{1-8}$alkoxy, halo$C_{1-8}$alkyl, $C_{3-6}$cycloalkyl, 5 membered heteroaryl, —C(O)NHR, —NHC(O)R, —S(O)$_2$NHR and —C≡CR;

each occurrence of R is independently selected from $C_{1-8}$alkyl, $C_{3-12}$cycloalkyl, and $C_{6-14}$aryl;

'm' is an integer ranging from 0 to 3, both inclusive; and

'n' is an integer ranging from 0 to 3, both inclusive;

with the proviso that 'm' and 'n' are not '0' simultaneously.

The compounds of formula (I) exhibit mPGES-1 enzyme inhibition activity and, therefore, are useful for the treatment of pain and inflammation in a variety of diseases or conditions.

The compound "N-(4-chloro-3-(5-oxo-1-(4-(trifluoromethyl)phenyl)-4,5-dihydro-1H-1,2,4-triazol-3-yl)benzyl)pivalamide", herein after designated as "compound of formula (II)" is disclosed as Example 100 in the specification of WO 2013/186692. Also disclosed therein, is the process for preparation of compound of formula (II). The structural representation of compound of formula (II) is

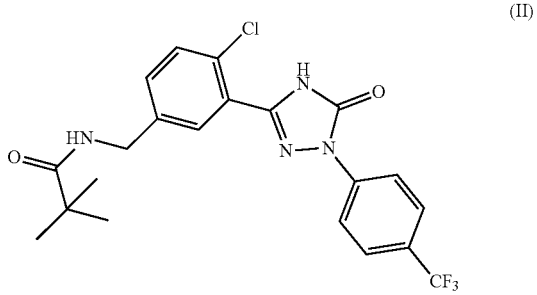 [SMILES: CC(C)(C)C(=O)NCc1ccc(Cl)c(-c2nn(-c3ccc(C(F)(F)F)cc3)c(=O)[nH]2)c1]

(II)

Development of a commercial drug candidate involves many steps, such as development of a cost effective synthetic method which is efficient in large scale manufacturing process. Also, in formulation of drug compositions, it is important for the active pharmaceutical ingredient to be in a form in which it can be conveniently handled and processed. Convenient handling is important not only from the perspective of obtaining a commercially viable manufacturing process, but also from the perspective of subsequent manufacture of pharmaceutical formulations comprising the active pharmaceutical ingredient. The drug development therefore involves research regarding finding suitable pharmaceutically acceptable salt forms of a drug. It may be also desirable to explore various polymorphs of the active pharmaceutical ingredient, which display better handling properties as well as it may also show improved physicochemical as well as pharmacokinetic and pharmacodynamics properties.

SUMMARY OF THE INVENTION

The present application relates to novel solid state forms of compound of formula (II). Further the present application relates to an improved process for the manufacture of compound of formula (II) which is suitable for large scale synthesis. The process of the present application involves less number of steps and also provides the compound of formula (II) in high yield and with high purity.

In one aspect, the present application relates to N-(4-chloro-3-(5-oxo-1-(4-(trifluoromethyl)phenyl)-4,5-dihydro-1H-1,2,4-triazol-3-yl)benzyl)pivalamide, represented by formula (II) in solid state form.

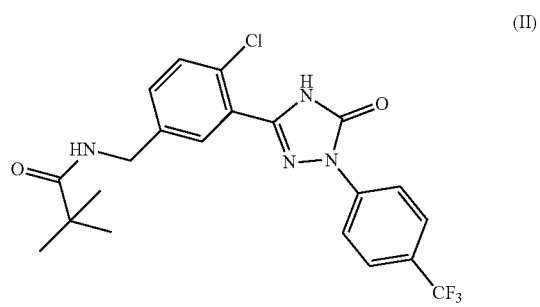 [SMILES: CC(C)(C)C(=O)NCc1ccc(Cl)c(-c2nn(-c3ccc(C(F)(F)F)cc3)c(=O)[nH]2)c1]

(II)

N-(4-chloro-3-(5-oxo-1-(4-(trifluoromethyl)phenyl)-4,5-dihydro-1H-1,2,4-triazol-3-yl)benzyl)pivalamide, herein after designated as compound of formula (II).

In an embodiment, the solid state forms of compound of formula (II) exist in an anhydrous and/or solvent-free form or as a hydrate and/or a solvate form.

In another embodiment, the present invention relates to crystalline form of compound of formula (II).

In another embodiment, the present invention relates to crystalline form of compound of formula (II) which is designated as Form I.

In yet another embodiment, the present invention relates to process for preparing crystalline form of compound of formula (II) which is designated as Form I.

In another embodiment the present invention relates to crystalline form of compound of formula (II) which is designated as Form II.

In yet another embodiment, the present invention relates to process for preparing crystalline form of compound of formula (II) which is designated as Form II.

In another embodiment the present invention relates to crystalline form of compound of formula (II) which is designated as Form III.

In yet another embodiment, the present invention relates to process for preparing crystalline form of compound of formula (II) which is designated as Form III.

In an embodiment of the present invention, the various crystalline forms of the invention are in substantially pure crystalline forms. For the purpose of the present invention, the term "substantially pure" as used herein includes reference to crystalline forms of, or greater than, 90%, more preferably 95%, more preferably 97%, more preferably 99% polymorphic purity as determined, for example by X-ray powder diffraction, Raman spectroscopy or IR spectroscopy.

In yet another embodiment the present invention relates to crystalline form of compound of formula (II), which is a mixture of any two or more forms of compound of formula (II), designated as Form I, Form II and Form III.

In another aspect of the application there is provided an amorphous form of N-(4-chloro-3-(5-oxo-1-(4-(trifluoromethyl)phenyl)-4,5-dihydro-1H-1,2,4-triazol-3-yl)benzyl)pivalamide (compound of formula (II)).

In yet another embodiment, the present invention relates to process for preparing compound of formula (II) in amorphous form.

In another embodiment, there is provided a method for treating diseases, conditions and/or disorders modulated by mPGES-1 enzyme; comprising administering a crystalline form of compound of formula (II), or a pharmaceutical composition that comprises the crystalline form of compound of formula (II) along with pharmaceutically acceptable excipients.

In another embodiment, there is provided a method for treating diseases, conditions and/or disorders modulated by mPGES-1 enzyme; comprising administering a crystalline form of compound of formula (II) designated as Form (I), or a pharmaceutical composition that comprises the crystalline form of compound of formula (II) designated as Form (I), along with pharmaceutically acceptable excipients.

In another embodiment, there is provided a method for treating diseases, conditions and/or disorders modulated by mPGES-1 enzyme; comprising administering a crystalline form of compound of formula (II) designated as Form (II), or a pharmaceutical composition that comprises the crystalline form of compound of formula (II) designated as Form (II), along with pharmaceutically acceptable excipients.

In another embodiment, there is provided a method for treating diseases, conditions and/or disorders modulated by mPGES-1 enzyme; comprising administering a crystalline form of compound of formula (II) designated as Form (III), or a pharmaceutical composition that comprises the crystalline form of compound of formula (II) designated as Form (III), along with pharmaceutically acceptable excipients.

In another embodiment, there is provided crystalline compound of formula (II) having an average particle size value ($D_{50}$) in the range from about 1 μm to about 100 μm.

In yet another embodiment, there is provided the crystalline compound of formula (II) having an average particle size value ($D_{50}$) in range from about 1 μm to about 50 μm.

In yet another embodiment, there is provided crystalline compound of formula (II) having an average particle size value ($D_{50}$) in the range from about 1 μm to about 20 μm.

In another embodiment, there is provided crystalline compound of formula (II) having a $D_{10}$ value in the range from about 0.3 μm to about 10 μm.

In yet another embodiment, there is provided crystalline compound of formula (II) having a $D_{10}$ value in the range from about 0.5 μm to about 8 μm.

In yet another embodiment, there is provided crystalline compound of formula (II) having a $D_{10}$ value in the range from about 0.5 μm to about 5 μm.

In another embodiment, there is provided crystalline compound of formula (II) having a $D_{90}$ value in the range from about 4 μm to about 300 μm.

In yet another embodiment, there is provided crystalline compound of formula (II) having a $D_{90}$ value in the range from about 5 μm to about 250 μm.

In yet another embodiment, there is provided crystalline compound of formula (II) having a $D_{90}$ value in the range from about 5 μm to about 200 μm.

In yet another embodiment, there is provided the compound of formula (II) having a $D_{90}$ value in the range from about 5 μm to about 150 μm.

In another aspect of the application there is provided substantially pure N-(4-chloro-3-(5-oxo-1-(4-(trifluoromethyl)phenyl)-4,5-dihydro-1H-1,2,4-triazol-3-yl)benzyl) pivalamide (compound of formula (II)). For the purpose of the present invention, the term "substantially pure" as used herein includes reference to purity of, or greater than, 98%, more preferably 99%, more preferably 99.5%, more preferably 99.9% purity as determined, for example by HPLC.

In yet another embodiment, the present invention relates to substantially pure compound of formula (II) having purity greater than about 98% by HPLC.

In yet another embodiment, the present invention relates to substantially pure compound of formula (II) having purity greater than about 99% by HPLC.

In yet another embodiment, the present invention relates to substantially pure compound of formula (II) having purity greater than about 99.9% by HPLC.

In yet another embodiment, three is provided compound of formula (II) which is substantially free from the impurity represented by compound of formula (II').

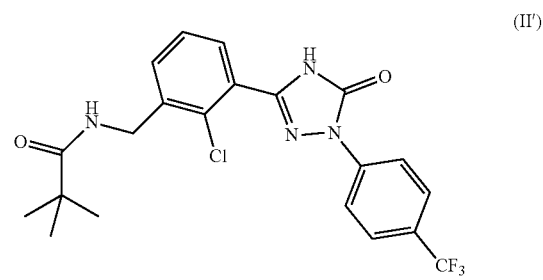 [SMILES: CC(C)(C)C(=O)NCc1cccc(-c2nn(-c3ccc(C(F)(F)F)cc3)c(=O)[nH]2)c1Cl]

For the purpose of this invention, the term "substantially free" as used herein includes reference to presence of impurity of, or less than, 2%, more preferably 1%, more preferably 0.5%, more preferably 0.1% impurity as determined, for example by HPLC.

In yet another aspect of the application, there is provided an improved process for preparation of compound of formula (II) or its pharmaceutically acceptable salts.

In an embodiment, the present application relates to process for preparation of compound of formula (II) or salt thereof

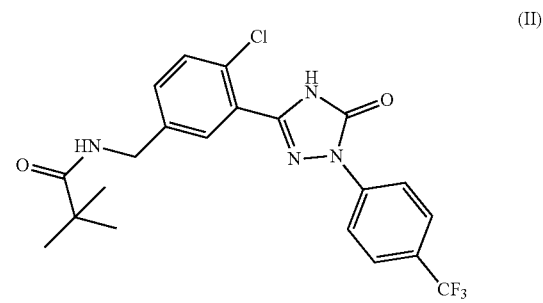 [SMILES: CC(C)(C)C(=O)NCc1ccc(Cl)c(-c2nn(-c3ccc(C(F)(F)F)cc3)c(=O)[nH]2)c1]

wherein the compound of formula (II) is prepared from compound of formula (III)

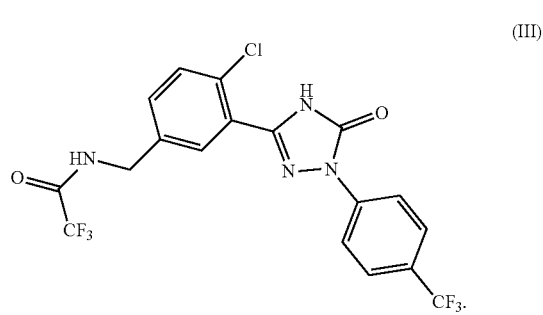 [SMILES: O=C(NCc1ccc(Cl)c(-c2nn(-c3ccc(C(F)(F)F)cc3)c(=O)[nH]2)c1)C(F)(F)F]

In yet another embodiment, there is provided process for preparation of compound of formula (II) or salt thereof, which process comprising the step of reacting compound of formula (IV)

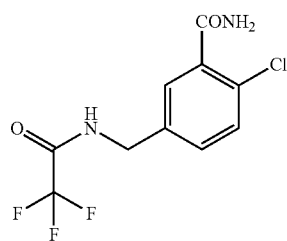

with oxalyl chloride and compound of formula (V)

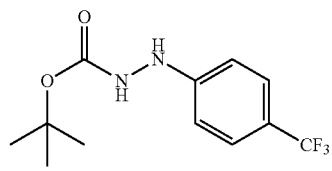

to obtain compound of formula (III)

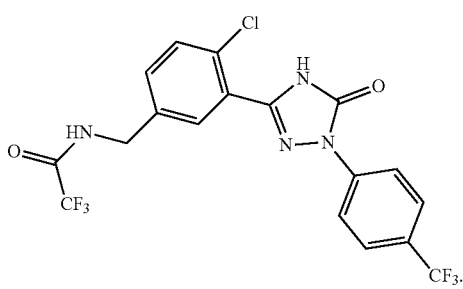

In yet another embodiment there is provided process for the preparation of compound of formula (II) or salt thereof, which process comprises the steps of:

a) reacting 2-chloro benzoic acid with 2,2,2-trifluoro-N-(hydroxymethyl)acetamide to obtain substantially pure compound of formula (VI);

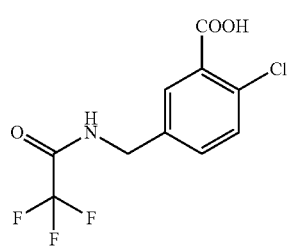

b) converting compound of formula (VI) to compound of formula (IV);

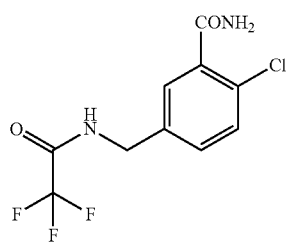

c) reacting compound of formula (IV) with oxalyl chloride and compound of formula (V)

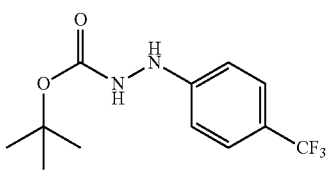

to obtain compound of formula (III);

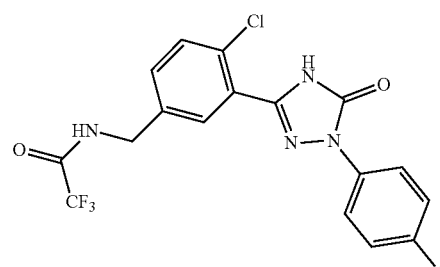

d) converting compound of formula (III) to compound of formula (II).

In another embodiment, there is provided process for preparation of compound of formula (II) or salt thereof, which process comprising the step of reacting 2-chloro benzoic acid with a compound (VII)

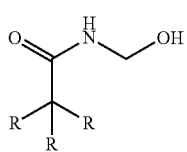

to obtain compound of formula (VIa)

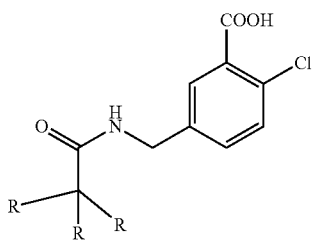

(VIa)

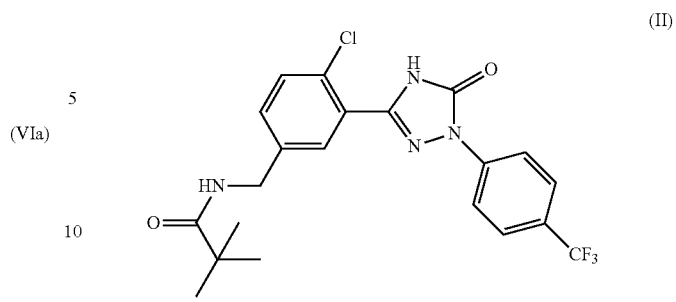

(II)

wherein R is chloro, bromo or methyl. In this embodiment, compound (VII) can be selected from 2,2,2-Trichloro-N-(hydroxymethyl)acetamide, 2,2,2-Tribromo-N-(hydroxymethyl) acetamide or 2,2,2-Trimethyl-N-(hydroxymethyl)acetamide.

BRIEF DESCRIPTION OF THE FIGURES

FIG. 1 is powder X-ray diffraction pattern of crystalline form of N-(4-chloro-3-(5-oxo-1-(4-(trifluoromethyl)phenyl)-4,5-dihydro-1H-1,2,4-triazol-3-yl)benzyl)pivalamide, designated as Form I.

FIG. 2 is Infra-Red (IR) spectra of crystalline form of N-(4-chloro-3-(5-oxo-1-(4-(trifluoromethyl)phenyl)-4,5-dihydro-1H-1,2,4-triazol-3-yl)benzyl)pivalamide, designated as Form I.

FIG. 3 is powder X-ray diffraction pattern of crystalline form of N-(4-chloro-3-(5-oxo-1-(4-(trifluoromethyl)phenyl)-4,5-dihydro-1H-1,2,4-triazol-3-yl)benzyl)pivalamide, designated as Form II.

FIG. 4 is Infra-Red (IR) spectra of crystalline form of N-(4-chloro-3-(5-oxo-1-(4-(trifluoromethyl)phenyl)-4,5-dihydro-1H-1,2,4-triazol-3-yl)benzyl)pivalamide, designated as Form II.

FIG. 5 is powder X-ray diffraction pattern of crystalline form of N-(4-chloro-3-(5-oxo-1-(4-(trifluoromethyl)phenyl)-4,5-dihydro-1H-1,2,4-triazol-3-yl)benzyl)pivalamide, designated as Form III.

FIG. 6 is Infra-Red (IR) spectra of crystalline form of N-(4-chloro-3-(5-oxo-1-(4-(trifluoromethyl)phenyl)-4,5-dihydro-1H-1,2,4-triazol-3-yl)benzyl)pivalamide, designated as Form III.

FIG. 7 is powder X-ray diffraction pattern of amorphous form of N-(4-chloro-3-(5-oxo-1-(4-(trifluoromethyl)phenyl)-4,5-dihydro-1H-1,2,4-triazol-3-yl)benzyl)pivalamide.

DETAILED DESCRIPTION OF THE INVENTION

In one aspect, the present application relates to N-(4-chloro-3-(5-oxo-1-(4-(trifluoromethyl)phenyl)-4,5-dihydro-1H-1,2,4-triazol-3-yl)benzyl)pivalamide, represented by formula (II) in solid state form.

In an embodiment, the solid state forms of compound of formula (II) exist in an anhydrous and/or solvent-free form or as a hydrate and/or a solvate form.

In another embodiment, the present invention relates to solid state form of compound of formula (II) which is crystalline.

In another embodiment, the present invention relates to crystalline form compound of formula (II) which is designated as Form I.

In yet another embodiment, the present invention relates to process for preparing crystalline form of compound of formula (II) which is designated as Form I.

In another embodiment the present invention relates to crystalline form of compound of formula (II) which is designated as Form II.

In yet another embodiment, the present invention relates to process for preparing crystalline form of compound of formula (II) which is designated as Form II.

In another embodiment the present invention relates to crystalline form of compound of formula (II) which is designated as Form III.

In yet another embodiment, the present invention relates to process for preparing crystalline form of compound of formula (II) which is designated as Form III.

In an embodiment of the present invention, the various crystalline forms of the invention are in substantially pure crystalline forms. For the purpose of the present invention, the term "substantially pure" as used herein includes reference to crystalline forms of, or greater than, 90%, more preferably 95%, more preferably 97%, more preferably 99% polymorphic purity as determined, for example by X-ray powder diffraction, Raman spectroscopy or IR spectroscopy.

In another aspect of the application there is provided N-(4-chloro-3-(5-oxo-1-(4-(trifluoromethyl)phenyl)-4,5-dihydro-1H-1,2,4-triazol-3-yl)benzyl)pivalamide (compound of formula (II)) in amorphous form.

In yet another embodiment, the present invention relates to process for preparing compound of formula (II) in amorphous form.

In yet another aspect of the application there is provided substantially pure N-(4-chloro-3-(5-oxo-1-(4-(trifluoromethyl)phenyl)-4,5-dihydro-1H-1,2,4-triazol-3-yl)benzyl) pivalamide (compound of formula (II)). For the purpose of the present invention, the term "substantially pure" as used herein includes reference to purity of, or greater than, 98%, more preferably 99%, more preferably 99.5%, more preferably 99.9% purity as determined, for example by HPLC.

In yet another embodiment, the present invention relates to substantially pure compound of formula (II) having purity greater than about 98% by HPLC.

In yet another embodiment, the present invention relates to substantially pure compound of formula (II) having purity greater than about 99% by HPLC.

In yet another embodiment, the present invention relates to substantially pure compound of formula (II) having purity greater than about 99.9% by HPLC.

In yet another embodiments provided compound of formula (II) which is substantially free from the impurity represented by compound of formula (II').

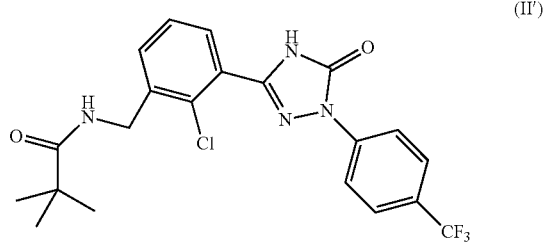 [SMILES: CC(C)(C)C(=O)NCc1cccc(-c2nn(-c3ccc(C(F)(F)F)cc3)c(=O)[nH]2)c1Cl]

For the purpose of this invention, the term "substantially free" as used herein includes reference to presence of impurity of, or less than, 2%, more preferably 1%, more preferably 0.5%, more preferably 0.1% impurity as determined, for example by HPLC.

In another embodiment, there is provided crystalline compound of formula (II) having an average particle size value ($D_{50}$) in the range from about 1 μm to about 100 μm.

In yet another embodiment, there is provided the crystalline compound of formula (II) having an average particle size value ($D_{50}$) in range from about 1 μm to about 50 μm.

In yet another embodiment, there is provided crystalline compound of formula (II) having an average particle size value ($D_{50}$) in the range from about 1 μm to about 20 μm.

In another embodiment, there is provided crystalline compound of formula (II) having a $D_{10}$ value in the range from about 0.3 μm to about 10 μm.

In yet another embodiment, there is provided crystalline compound of formula (II) having a $D_{10}$ value in the range from about 0.5 μm to about 8 μm.

In yet another embodiment, there is provided crystalline compound of formula (II) having a $D_{10}$ value in the range from about 0.5 μm to about 5 μm.

In another embodiment, there is provided crystalline compound of formula (II) having a $D_{90}$ value in the range from about 4 μm to about 300 μm.

In yet another embodiment, there is provided crystalline compound of formula (II) having a $D_{90}$ value in the range from about 5 μm to about 250 μm.

In yet another embodiment, there is provided crystalline compound of formula (II) having a $D_{90}$ value in the range from about 5 μm to about 200 μm.

In yet another embodiment, there is provided the compound of formula (II) having a $D_{90}$ value in the range from about 5 μm to about 150 μm.

The particle size characteristic for compound of formula (II) for some of the batches is provided in Table 1.

TABLE 1

| Batch. No | Particle size | | |
|---|---|---|---|
| | d (0.1) μm | d (0.5) μm | d (0.9) μm |
| 1 | 0.7 | 3.7 | 12.7 |
| 2 | 0.6 | 2.0 | 9.0 |
| 3 | 0.7 | 3.3 | 14.8 |

TABLE 1-continued

| Batch. No | Particle size | | |
|---|---|---|---|
| | d (0.1) μm | d (0.5) μm | d (0.9) μm |
| 4 | 0.7 | 2.4 | 10.7 |
| 5 | 0.7 | 2.2 | 9.4 |

In another embodiment, the present invention relates to crystalline form of compound of formula (II) which is designated as Form I.

In yet another embodiment, Form I of compound of formula (II) is characterized by the X-Ray Powder Diffraction (XRPD) pattern as shown in FIG. 1.

In yet another embodiment, Form I of compound of formula (II) is further characterized by the characteristic X-ray diffraction pattern comprising of the following peaks expressed in terms of 2θ±0.2: 5.66, 6.55 and 13.05.

In yet another embodiment, Form I of compound of formula (II) is further characterized by the characteristic X-ray diffraction pattern comprising of the following peaks expressed in terms of 2θ±0.2: 5.66, 6.55, 12.51, 13.05, 15.01, 16.59 and 25.69.

In yet another embodiment, Form I of compound of formula (II) is further characterized by the characteristic X-ray diffraction pattern peaks expressed in terms of 2θ as presented in Table 2.

TABLE 2

Prominent two theta positions and relative intensities of XRPD of Form I of compound of formula (II)

| Angle (2θ ± 0.2) | Relative intensity (%) |
|---|---|
| 5.07 | 21.13 |
| 5.66 | 28.35 |
| 6.55 | 7.22 |
| 6.99 | 41.72 |
| 8.82 | 29.52 |
| 12.51 | 100.00 |
| 13.05 | 11.12 |
| 14.48 | 6.01 |
| 15.01 | 17.96 |
| 16.59 | 42.13 |
| 16.81 | 29.64 |
| 17.56 | 6.69 |
| 18.28 | 24.69 |
| 20.00 | 7.05 |
| 20.53 | 11.23 |
| 21.59 | 9.41 |
| 22.55 | 9.42 |
| 24.46 | 7.20 |
| 25.69 | 24.98 |
| 26.14 | 9.03 |
| 26.45 | 9.27 |
| 27.07 | 8.83 |
| 28.23 | 7.56 |

In yet another embodiment, Form I of compound of formula (II) is characterized by the Fourier Transform Infrared Spectroscopy (FT-IR) pattern as shown in FIG. 2.

In another embodiment, the present invention relates to crystalline form of compound of formula (II) which is designated as Form II.

In yet another embodiment, Form II of compound of formula (II) is characterized by the X-Ray Powder Diffraction (XRPD) pattern as shown in FIG. 3.

In yet another embodiment, Form II of compound of formula (II) is further characterized by the characteristic X-ray diffraction pattern comprising of the following peaks expressed in terms of 2θ±0.2: 24.57 and 30.85.

In yet another embodiment, Form II of compound of formula (II) is further characterized by the characteristic X-ray diffraction pattern comprising of the following peaks expressed in terms of 2θ±0.2: 7.02, 12.54, 16.64, 18.31, 24.57, 25.74 and 30.85.

In yet another embodiment, Form II of compound of formula (II) is further characterized by the characteristic X-ray diffraction pattern peaks expressed in terms of 2θ as presented in Table 3.

TABLE 3

Prominent two theta positions and relative intensities of XRPD of Form II of compound of formula (II)

| Angle (2θ ± 0.2) | Relative intensity (%) |
|---|---|
| 5.07 | 13.40 |
| 7.02 | 22.82 |
| 8.85 | 12.97 |
| 12.54 | 79.59 |
| 14.50 | 10.18 |
| 15.05 | 14.36 |
| 16.64 | 100.00 |
| 16.92 | 13.77 |
| 18.31 | 27.64 |
| 20.03 | 20.28 |
| 20.56 | 15.10 |
| 20.83 | 17.87 |
| 21.59 | 10.93 |
| 22.59 | 11.52 |
| 24.44 | 9.45 |
| 24.57 | 10.01 |
| 25.06 | 5.63 |
| 25.74 | 34.24 |
| 26.22 | 13.36 |
| 26.43 | 7.29 |
| 27.07 | 9.21 |
| 27.97 | 7.49 |
| 28.25 | 7.44 |
| 30.85 | 5.62 |

In yet another embodiment, Form II of compound of formula (II) is characterized by the Fourier Transform Infrared Spectroscopy (FT-IR) pattern as shown in FIG. 4.

In another embodiment, the present invention relates to crystalline form of compound of formula (II) which is designated as Form III.

In yet another embodiment, Form III of compound of formula (II) is characterized by the X-Ray Powder Diffraction (XRPD) pattern as shown in FIG. 5.

In yet another embodiment, Form III of compound of formula (II) is further characterized by the characteristic X-ray diffraction pattern comprising of the following peaks expressed in terms of 2θ±0.2: 13.92, 31.01, 35.13 and 38.54.

In yet another embodiment, Form III of compound of formula (II) is further characterized by the characteristic X-ray diffraction pattern comprising of the following peaks expressed in terms of 2θ±0.2: 7.00, 12.60, 13.92, 16.71, 20.89, 24.55, 31.01, 35.13 and 38.54.

In yet another embodiment, Form III of compound of formula (II) is further characterized by the characteristic X-ray diffraction pattern peaks expressed in terms of 2θ as presented in Table 4.

TABLE 4

Prominent two theta positions and relative intensities of XRPD of Form III of compound of formula (II)

| Angle (2θ ± 0.2) | Relative intensity (%) |
|---|---|
| 7.00 | 100.00 |
| 8.86 | 21.61 |
| 12.60 | 37.24 |
| 13.92 | 11.19 |
| 14.53 | 21.77 |
| 15.10 | 64.50 |
| 16.71 | 41.21 |
| 17.62 | 11.10 |
| 18.31 | 8.42 |
| 20.89 | 48.85 |
| 21.70 | 13.65 |
| 22.16 | 12.85 |
| 22.69 | 6.91 |
| 23.65 | 3.55 |
| 24.55 | 20.52 |
| 25.29 | 5.10 |
| 25.83 | 8.92 |
| 26.55 | 9.56 |
| 27.18 | 6.86 |
| 27.94 | 15.23 |
| 31.01 | 5.22 |
| 35.13 | 6.07 |
| 38.54 | 5.67 |

In yet another embodiment, Form III of compound of formula (II) is characterized by the Fourier Transform Infrared Spectroscopy (FT-IR) pattern as shown in FIG. 6.

In another embodiment, the present invention relates to an amorphous form of compound of formula (II).

In yet another embodiment, amorphous form of compound of formula (II) is characterized by the X-Ray Powder Diffraction (XRPD) pattern as shown in FIG. 7.

In another aspect, the present invention relates to process for preparing crystalline form of compound of formula (II) which is designated as Form I.

The process to prepare Form I comprises taking the compound of formula (II) in a mixture of diethyl ether and methanol. Alternatively, the compound of formula (II) can be taken in a mixture of methyl tert-butyl ether and methanol. Preferably, the compound of formula (II) can be taken in the mixture of solvent under inert atmosphere. The reaction mass may be stirred at a suitable temperature for a suitable period of time. The suitable temperature may be about 20 to 40° C., preferably about 25 to 30° C. The suitable period may be up to 5 hours, preferably about 1-2 hours. The solid may be collected by methods including decantation, centrifugation, gravity filtration, suction filtration, or any other technique for the isolation of solids. In a preferred embodiment, the solid may be filtered and washed with diethyl ether or methyl tert-butyl ether.

The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity limit of LOD is achieved. For example, it may vary from about 1 to about 10 hours or longer.

In another aspect, the present invention relates to process for preparing crystalline form of compound of formula (II) which is designated as Form II.

The process to prepare Form II comprises heating the compound of formula (II) to melt by external heating source such as heating mantle. The temperature for heating may be about 150-300° C., preferably about 200° C. The reaction mass may be cooled slowly to a suitable temperature to obtain crystalline form of compound of formula (II) which is designated as Form II. The suitable temperature to which the reaction mass may be cooled may be in the temperature range of 20-50° C., preferably 25-30° C.

Alternatively, crystalline form of compound of formula (II) which is designated as Form II can be obtained by the process, which process comprises taking the compound of formula (II) in ethyl acetate. The compound of formula (II) may also be taken in a mixture of ethyl acetate and methanol. Preferably, the compound of formula (II) can be taken in the solvent or mixture of solvents under inert atmosphere. The reaction mass may be stirred at a suitable temperature for a suitable period of time. The suitable temperature may be about 20 to 40° C., preferably about 25 to 30° C. The suitable period may be up to 5 hours, preferably about 1-2 hours. The solid may be collected by methods including decantation, centrifugation, gravity filtration, suction filtration, or any other technique for the isolation of solids. The recovered solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity is achieved. For example, it may vary from about 1 to about 10 hours or longer.

In another aspect, the present invention relates to a process for preparing crystalline form of compound of formula (II) which is designated as Form III.

The process to prepare Form III comprises taking the compound of formula (II) in tetrahydrofuran. Preferably, the compound of formula (II) can be taken in the solvent under inert atmosphere. The reaction mass may be stirred at a suitable temperature. The suitable temperature may be about 20 to 40° C., more preferably about 25 to 30° C. The reaction mass may be stirred for a suitable period of time. The suitable period may be up to 1 hour, preferably about 10-15 minutes. To the reaction mixture, a non-polar solvent may be added. The non-polar solvent may be any hydrocarbon solvent such as n-heptane, n-hexane or n-pentane. The reaction mixture may be further stirred at a suitable temperature for suitable period of time. The suitable temperature may be about 20 to 40° C., more preferably about 25 to 30° C. The suitable period may be up to 10 hours, preferably about 3-4 hours. The solid may be collected by methods including decantation, centrifugation, gravity filtration, suction filtration, or any other technique for the isolation of solids. In a preferred embodiment, the solid may be filtered and washed with n-heptane. The isolated solid may be optionally further dried. Drying may be carried out in a tray dryer, vacuum oven, air oven, fluidized bed drier, spin flash dryer, flash dryer, or the like. The drying may be carried out at atmospheric pressure or under a reduced pressure at suitable temperatures as long as the compound of formula (II) is not degraded in quality. The drying may be carried out for any desired time until the required purity limit of LOD is achieved. For example, it may vary from about 1 to about 10 hours or longer.

In another aspect, the present invention relates to a process for preparing compound of formula (II) in amorphous form.

The process comprises heating the compound of formula (II) to melt by external heating device such as heating mantle. The temperature for heating may be about 150-300° C., preferably about 200° C. The reaction mass may be cooled rapidly to a suitable temperature to obtain the compound of formula (II) in amorphous form. The suitable temperature to which the compound may be cooled may be in the temperature range of 20-50° C., preferably 25-30° C.

In another aspect of the invention, there is provided a pharmaceutical composition comprising an excipients, carriers, diluents or mixture thereof, and therapeutically acceptable amount of crystalline compound of formula (II) designated as Form (I).

In another embodiment of the invention, there is provided a method of treating diseases, conditions and/or disorders modulated by mPGES-1 enzyme; comprising administering a crystalline form of compound of formula (II) designated as Form (I), or a pharmaceutical composition that comprises the crystalline form of compound of formula (II) designated as form (I) along with pharmaceutically acceptable excipients.

In another embodiment of the invention, there is provided a pharmaceutical composition comprising an excipients, carriers, diluents or mixture thereof, and therapeutically acceptable amount of crystalline compound of formula (II) designated as Form (II).

In another embodiment of the invention, there is provided a method of treating diseases, conditions and/or disorders modulated by mPGES-1 enzyme; comprising administering a crystalline form of compound of formula (II) designated as Form (II), or a pharmaceutical composition that comprises the crystalline form of compound of formula (II) designated as form (II) along with pharmaceutically acceptable excipients.

In another embodiment of the invention, there is provided a pharmaceutical composition comprising an excipients, carriers, diluents or mixture thereof, and therapeutically acceptable amount of crystalline compound of formula (II) designated as Form (III).

In another embodiment of the invention, there is provided a method of treating diseases, conditions and/or disorders modulated by mPGES-1 enzyme; comprising administering a crystalline form of compound of formula (II) designated as Form (III), or a pharmaceutical composition that comprises the crystalline form of compound of formula (II) designated as form (III) along with pharmaceutically acceptable excipients.

In another embodiment, the present invention pertains to a method of treating diseases or conditions or disorders associated with mPGES-1 enzyme, which are selected from inflammation, asthma, chronic obstructive pulmonary disease, pulmonary fibrosis, inflammatory bowel disease, irritable bowel syndrome, pain, inflammatory pain, chronic pain, acute pain, fever, migraine, headache, low back pain, fibromyalgia, myofascial disorders, viral infections, influenza, common cold, herpes zoster, hepatitis C, AIDS, bacterial infections, fungal infections, dysmenorrhea, burns, surgical or dental procedures, malignancies hyperprostaglandin E syndrome, classic Bartter syndrome, synovitis, atherosclerosis, gout, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, cancer, neurodegenerative disorders such as Alzheimer's disease, Parkinson's disease, Amyotrophic lateral sclerosis and multiple sclerosis, autoimmune diseases, allergic disorders, rhinitis, ulcers, mild to moderately active ulcerative colitis, familial adenomatous polyposis, coronary heart disease, and sarcoidosis by administering crystalline compound of formula (II) designated as Form (I), Form (II) or Form (III).

In yet another embodiment, the present invention pertains to a method of treating diseases or conditions or disorders associated with mPGES-1 enzyme, which is selected from of pain, chronic pain, acute pain, rheumatoid arthritis pain or osteoarthritic pain by administering crystalline compound of formula (II), designated as Form (I), Form (II) or Form (III), in therapeutically effective amount.

In yet another embodiment, the present invention pertains to a method of treating pain, chronic pain, acute pain, rheumatoid arthritis pain or osteoarthritic pain by administering crystalline compound of formula (II), designated as Form (I), Form (II) or Form (III), in therapeutically effective amount.

In yet another embodiment, the present invention pertains to a method of treating inflammation, neurodegenerative disorders such as Parkinson's disease, Alzheimer's disease and amyotrophic lateral sclerosis by administering crystalline compound of formula (II), designated as Form (I), Form (II) or Form (III), in therapeutically effective amount.

In another embodiment, there is provided process for the preparation of compound of formula (II) which process comprises the steps as shown in the scheme 1.

Scheme 1:

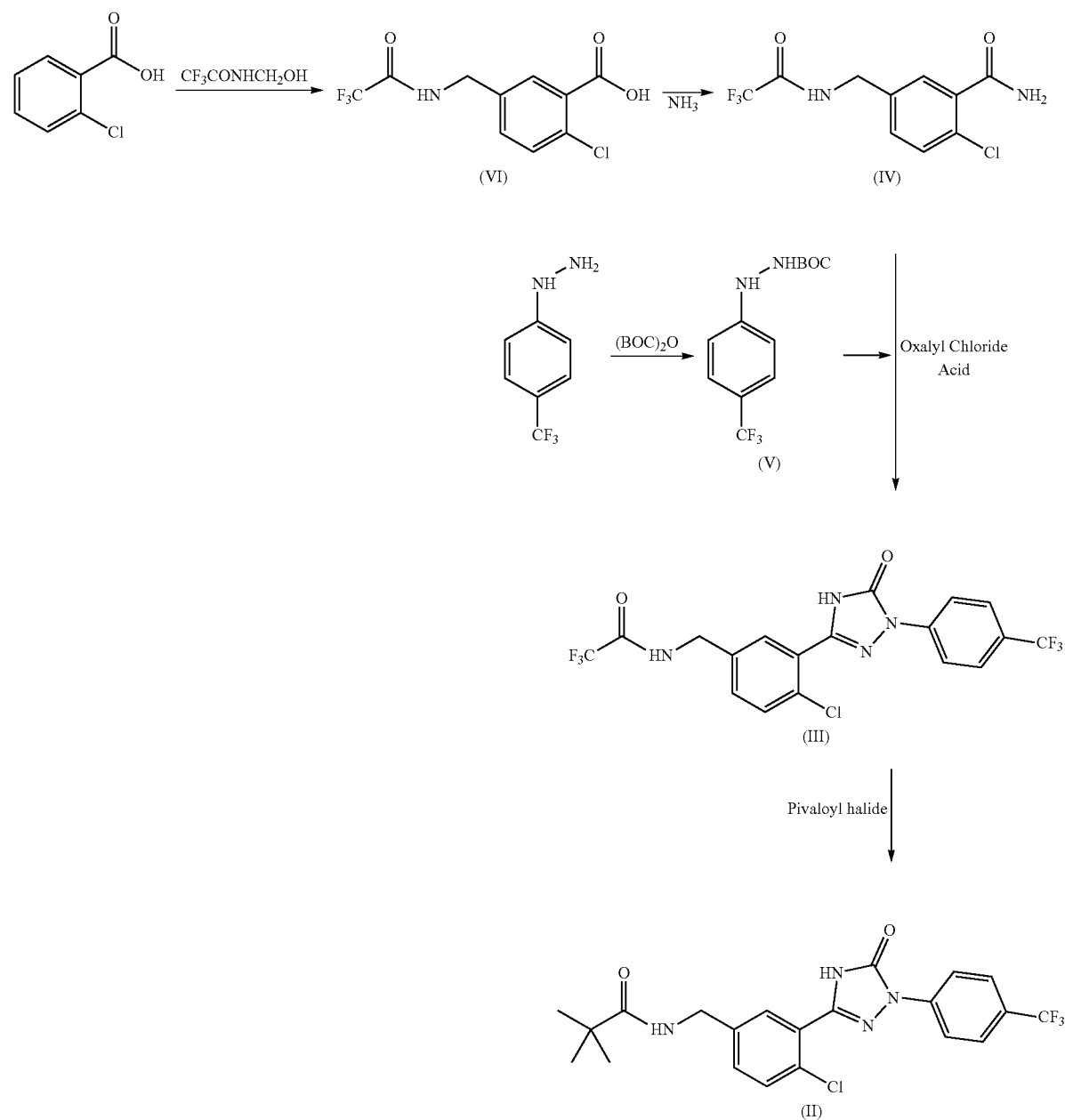

The process to prepare compound of formula (II) comprises:

a) reacting 2-chloro benzoic acid with 2,2,2-trifluoro-N-(hydroxymethyl)acetamide to obtain substantially pure compound of formula (VI);

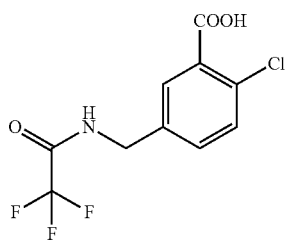

(VI)

b) converting compound of formula (VI) to compound of formula (IV);

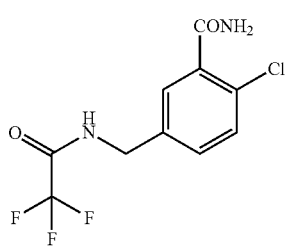

(IV)

c) reacting compound of formula (IV) with oxalyl chloride and compound of formula (V)

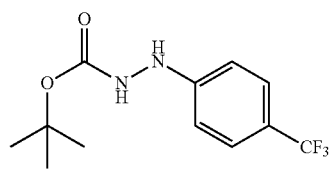

(V)

to obtain compound of formula (III)

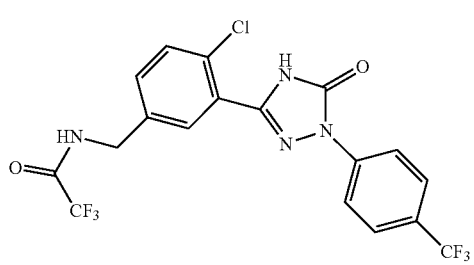

(III)

and d) converting compound of formula (III) to compound of formula (II)

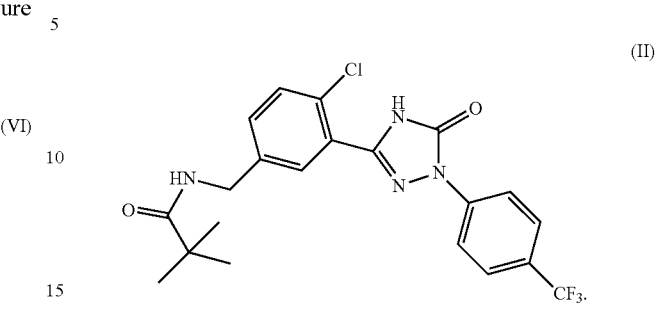

(II)

Step (a) involves reacting 2-chloro benzoic acid with 2,2,2-trifluoro-N-(hydroxymethyl)acetamide to obtain compound of formula (VI). The reaction may be carried out in presence of an acid. The acid may be inorganic or organic acid. Preferably, the acid may be inorganic acid. More preferably, the acid is sulphuric acid ($H_2SO_4$). The reaction may be carried out at a suitable temperature. The suitable temperature may be about 20-50° C., preferably 25-30° C.

After the completion of the reaction, the reaction mass may be poured into water to obtain a solid product, which may be filtered and dried. The solid product may be further purified by taking the product in a suitable solvent or mixture of solvents thereof. The suitable solvent may include, but not limited to, hydrocarbon solvents such as toluene, xylene, n-heptane, cyclohexane and n-hexane and/or ether solvent such as methyl ethyl ketone. Preferably, the suitable solvent(s) is toluene and/or methyl ethyl ketone. The mixture may be optionally heated till a clear solution is obtained. The clear solution may be cooled to obtain the solid which may be filtered and dried. The purification step may be further repeated to obtain a product of desired purity.

Step (b) involves converting compound of formula (VI) to compound of formula (IV). The compound of formula (VI) is treated with an activating agent to form its activated carboxylic acid derivative, followed by treatment with a source of ammonia to obtain compound of formula (IV).

In an embodiment, the compound of formula (VI) may be first treated with an activating agent to form its activated carboxylic acid derivative. The activating agent includes, but not limited to, oxalyl chloride, thionyl chloride, phosphorous trichloride, phosphorous pentachloride and the like. Preferably the activating agent is oxalyl chloride. The reaction of compound of formula (VI) with an activating agent may be catalysed by adding a suitable reagent such as DMF or triethyl amine. In an embodiment, the catalysing reagent is DMF. The reaction may be carried out in a suitable solvent. The suitable solvent may be a polar solvent. Preferably the solvent is tetrahydofuran. In another embodiment, the reaction mixture may be stirred at a suitable temperature for a suitable period of time. The suitable temperature may be about 25-30° C. The suitable time period may be 2-4 hours. After the completion of the reaction, the reaction mass may be subjected to evaporation to distil out the excess of solvent to obtain activated carboxylic acid derivative of compound of formula (VI).

The activated carboxylic acid derivative of compound of formula (VI) may be further treated with a source of ammonia to obtain compound of formula (IV). The source of ammonia includes, but not limited to, formamide, ammonia gas, aqueous ammonia, alcoholic ammonia and the like.

Preferably the source of ammonia is ammonia gas. The reaction may be carried out in any polar solvent. Preferably the solvent is tetrahydofuran. In an embodiment, the ammonia gas may be purged in the reaction mixture. The reaction mixture may be stirred at a suitable temperature for a suitable period of time. The suitable temperature may be about 25-30° C. The suitable period of time may be 1-2 hours. The reaction mixture may be maintained at a suitable pH. The suitable pH may be about 7-9.

After the completion of the reaction, the reaction may be quenched with water, and the reaction mass may be extracted with a suitable solvent. The suitable solvent for extraction may be ethyl acetate. The organic layer may be dried and evaporated to dryness to obtain a product. The product obtained may be taken in a non-polar solvent and stirred. The non-polar solvent may be any hydrocarbon solvent. Preferably the solvent is cyclohexane. The product may be filtered and dried to obtain the compound of formula (IV).

Step (c) involves reacting compound of formula (IV) with oxalyl chloride and compound of formula (V) to obtain compound of formula (III).

The compound of formula (IV) may be first reacted with oxalyl chloride. The reaction may be carried out in a halogenated solvent. The halogenated solvent may be methylene dichloride, ethylene dichloride, chloroform or carbon tetrachloride. Preferably the halogenated solvent is methylene dichloride. The reaction mixture may be heated to a suitable temperate for a suitable period of time. The suitable temperature may be about 45-50° C. The suitable time period may be 4-24 hours. The excess solvent in the reaction mixture may be evaporated under the reduced pressure to obtain a residue. A solution of compound of formula (V) in a halogenated solvent may be added to the residue. The halogenated solvent may methylene dichloride, ethylene dichloride, chloroform or carbon tetrachloride. Preferably the halogenated solvent is methylene dichloride. The reaction mixture may be stirred at a suitable temperature for a suitable period of time. In another embodiment, the temperature of the reaction may be about 15-20° C. In yet another embodiment the reaction may be stirred for about 4-6 hours.

The reaction mixture may be further treated with an acid. The acid may be an organic acid. Preferably the organic acid is trifluoroacetic acid. The reaction mixture may be stirred at a suitable temperature for a suitable period of time. The suitable temperature may be about 25-30° C. The suitable time period may be about 15-20 hours. After the completion of the reaction, a suitable solvent may be added to the reaction mixture. The suitable solvent may be a non-polar solvent. The non-polar solvent may be any hydrocarbon solvent. Preferably the hydrocarbon solvent is cyclohexane. The reaction mixture may be maintained at a suitable temperate for a suitable period of time. The suitable temperature may be about 25-30° C. The suitable time period may be 1-2 hours. The precipitate obtained may be filtered and dried to obtain compound of formula (III). Optionally, the product may be further taken in a suitable solvent to obtain a clear solution. The suitable solvent may be any polar solvent. Preferably, the polar solvent is tetrahydrofuran. The temperature range for the process may be about 65-70° C. Another suitable non-polar solvent may be charged to the clear solution. The suitable solvent may be a non-polar solvent. The non-polar solvent may be any hydrocarbon solvent. Preferably the hydrocarbon solvent is cyclohexane. The solution may be cooled to room temperature and the product precipitated may be filtered and washed with a suitable non-polar solvent such as cyclohexane to obtain compound of formula (III). The purification step may be further repeated to obtain the product of desired purity.

The compound of formula (V) may be prepared by reacting 4-(trifluoromethyl)phenylhydrazine or its suitable salt such as hydrochloride with di tert butyl dicarbonate. The hydrazine compound may be taken in a suitable solvent or mixture of solvents in which the compound is soluble. The suitable solvent may be water and polar solvent. Preferably the polar solvent is tetrahydrofuran. The reaction may be carried out in presence of mixture of water and tetrahydrofuran. The reaction may be carried out in the presence of a suitable base. The suitable base may be any inorganic base. The inorganic base may be sodium carbonate, potassium carbonate or lithium carbonate. Preferably, the inorganic base is sodium carbonate.

The reaction mixture may be stirred at a suitable temperature for a suitable period of time. The suitable temperature of the reaction may be room temperature (25-30° C.). The suitable period of time may be about 5-7 hours. The reaction mixture may be extracted with suitable solvent. The suitable solvent may be ethyl acetate. The organic layer may be dried and evaporated to dryness to obtain a product. The product obtained may be taken in a non-polar solvent. The non-polar solvent may be any hydrocarbon solvent. Preferably the solvent is cyclohexane. The product may be filtered and dried to obtain compound of formula (V). Optionally the product may be further washed with another solvent such as pentane to obtain the desired purity.

Step (d) involves reacting compound of formula (III) with pivaloyl halide to obtain compound of formula (II). In an embodiment, compound of formula (III) may be reacted with pivaloyl chloride. The reaction may be carried out in the presence of a suitable base. The suitable base may be any inorganic base. The inorganic base may be sodium hydroxide, potassium hydroxide or lithium hydroxide. Preferably, the inorganic base is sodium hydroxide. The reaction may be carried out in a suitable solvent or mixture of solvents. The suitable solvent may be water and any polar solvent. Preferably the polar solvent is tetrahydrofuran. The reaction may be carried out in presence of mixture of tetrahydrofuran and water.

In an embodiment, the compound of formula (III) may be first treated with the base at a suitable temperature. The suitable temperature may be 0-5° C. The reaction mass be stirred at a suitable temperature for a suitable period of time. The suitable temperature may be about 10-20° C. The suitable period may be 1-2 hour(s). The reaction mixture may be cooled to a suitable temperature and pivaloyl halide is added to it slowly. The suitable temperature may be 0-5° C. The reaction mass may be maintained at a suitable temperature for a suitable period of time. The suitable temperature may be about 0-5° C. The suitable period may be 30-60 minutes. To the reaction mixture conc. HCl or 10% NaOH solution may be optionally added to adjust the pH at 6-7 and the reaction mixture may be further stirred. The product precipitated may be filtered to obtain compound of formula (II). Optionally, the compound of formula (II) may be purified using another suitable solvent. The suitable solvent may be IPA. The compound and solvent mixture may be heated to obtain a clear solution. The solution may be cooled, precipitate obtained may be filtered and dried to obtain compound of formula (II) with enhanced purity. The purification step may be further repeated to obtain the desired purity.

In yet another aspect of the application there is provided process for preparation of compound of formula (II)

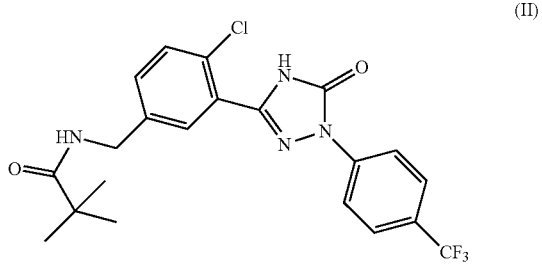 [SMILES: CC(C)(C)C(=O)NCc1ccc(Cl)c(-c2nn(-c3ccc(C(F)(F)F)cc3)c(=O)[nH]2)c1]

(II)

from compound of formula (III)

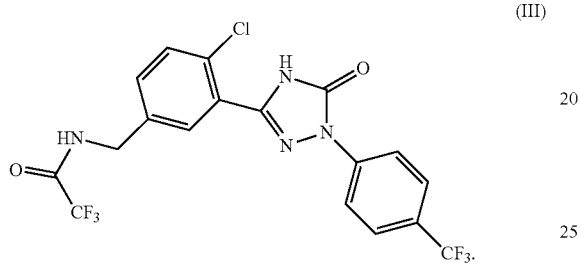

(III)

In an embodiment, there is provided process for preparation of compound of formula (II), which process comprises reacting compound of formula (III) with pivaloyl halide to obtain compound of formula (II).

In an embodiment, the compound of formula (III) may be reacted with pivaloyl chloride. The reaction may be carried out in presence of a suitable base. The suitable base may be an inorganic base. The inorganic base may be sodium hydroxide, potassium hydroxide or lithium hydroxide. Preferably, the inorganic base is sodium hydroxide. The reaction may be carried out in a suitable solvent or mixture of solvents. The suitable solvent may be water and polar solvent. Preferably the polar solvent is tetrahydrofuran. The reaction may be carried out in presence of water and tetrahydrofuran.

In another embodiment, the compound of formula (III) may be first treated with the water and base at a suitable temperature. The suitable temperature may be 0-5° C. The reaction mass be stirred at a suitable temperature for a suitable period of time. The suitable temperature may be about 10-20° C. The suitable period may be 1-2 hour(s). The reaction mixture may be cooled to a suitable temperature and pivaloyl halide may be added to it slowly. The suitable temperature may be 0-5° C. The reaction mass be maintained at a suitable temperature for a suitable period of time. The suitable temperature may be about 0-5° C. The suitable period may be 30-60 minutes. To the reaction mixture conc. HCl or 10% NaOH solution may be optionally added to adjust the pH at 6-7 and the reaction mixture may be further stirred. The product precipitated may be filtered and dried to obtain compound of formula (II). Optionally, the compound of formula (II) may be purified using a suitable solvent. The suitable solvent may be IPA. The compound and solvent mixture may be heated to obtain a clear solution. The solution may be cooled, precipitate obtained may be filtered and dried to obtain compound of formula (II) with enhanced purity. The purification step may be further repeated to obtain the desired purity.

In yet another embodiment, there is provided a process for preparation of compound of formula (II), which process comprising reacting compound of formula (IV)

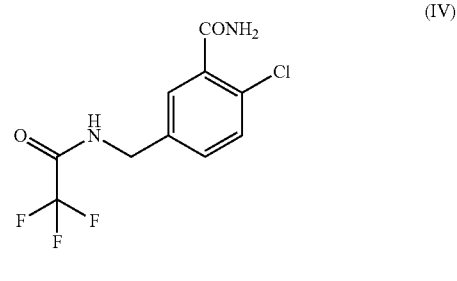 [SMILES: NC(=O)c1cc(CNC(=O)C(F)(F)F)ccc1Cl]

(IV)

with oxalyl chloride and compound of formula (V)

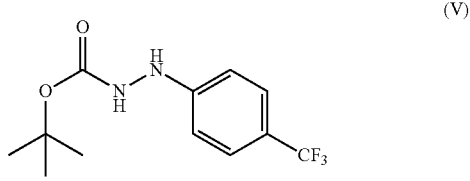 [SMILES: CC(C)(C)OC(=O)NNc1ccc(C(F)(F)F)cc1]

(V)

to obtain compound of formula (III).

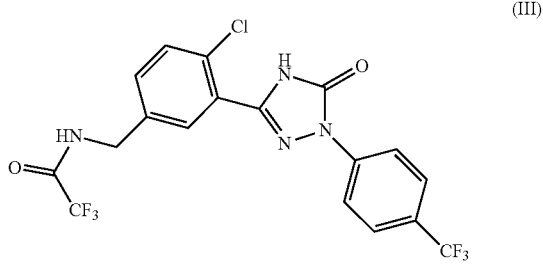 [SMILES: O=C(NCc1ccc(Cl)c(-c2nn(-c3ccc(C(F)(F)F)cc3)c(=O)[nH]2)c1)C(F)(F)F]

(III)

In an embodiment, the process involves reacting compound of formula (IV) with oxalyl chloride followed by reaction with compound of formula (V).

In another embodiment, the compound of formula (IV) may be first treated with oxalyl chloride. In this embodiment the reaction may be carried at temperature about 45-50° C. In another embodiment, the reaction may be stirred for 4-5 hours. The reaction may be carried in a halogenated solvent. The halogenated solvent may methylene dichloride, ethylene dichloride, chloroform or carbon tetrachloride. Preferably the halogenated solvent is methylene dichloride. The excess solvent in the reaction mixture may be evaporated under the reduced pressure to obtain a residue. A solution of compound of formula (V) in a suitable solvent may be added to the above reaction mixture. The suitable solvent may be a halogenated solvent. The halogenated solvent may be methylene dichloride, ethylene dichloride, chloroform or carbon tetrachloride. Preferably the halogenated solvent is methylene dichloride. The reaction mixture may be further stirred at a suitable temperature for a suitable period of time. In this embodiment, the temperature of the reaction may be about 15-20° C. and the reaction may be stirred for about 4-6 hours.

The reaction mixture may be further treated with an acid. The acid may be an organic acid. Preferably the organic acid is trifluoroacetic acid. The reaction mixture may be stirred at a suitable temperature for another suitable period of time. The suitable temperature may be about 25-30° C. The suitable time period may be about 15-20 hours. After the completion of the reaction, a suitable solvent may be added to the reaction mixture. The suitable solvent may be a non-polar solvent. The non-polar solvent may be any hydrocarbon solvent. Preferably the hydrocarbon solvent is cyclohexane. The reaction may be maintained at a suitable temperate for a suitable period of time. The suitable temperature may be about 25-30° C. The suitable period of time may be 1-2 hours. The precipitate obtained may be filtered and dried to obtain compound of formula (III). Optionally, the product may be further taken in a suitable solvent to obtain a clear solution. The suitable solvent may be any polar solvent. Preferably, the polar solvent is tetrahydrofuran. The temperature range for the process may be 65-70° C. A suitable non-polar solvent may be charged to the clear solution. The suitable solvent may be a non-polar solvent. The non-polar solvent may be any hydrocarbon solvent. Preferably the hydrocarbon solvent is cyclohexane. The solution may be cooled to room temperature and the compound precipitated may be filtered and washed with a suitable non-polar solvent such as cyclohexane to obtain compound of formula (III). The purification step may be further repeated to obtain the desired purity.

The compound of formula (V) may be prepared by reacting 4-(trifluoromethyl)phenylhydrazine or its suitable salt such as hydrochloride with di tert butyl dicarbonate. The hydrazine compound may be taken in a suitable solvent or mixture of solvents in which the compound is soluble. The suitable solvent may be water and polar solvent. Preferably the polar solvent is tetrahydrofuran. The reaction may be carried out in presence of mixture of water and tetrahydrofuran. The reaction may be carried out in the presence of a suitable base. The suitable base may be any inorganic base. The inorganic base may be sodium carbonate, potassium carbonate or lithium carbonate. Preferably, the inorganic base is sodium carbonate.

The reaction mixture may be stirred at a suitable temperature for a suitable period of time. The suitable temperature of the reaction may be room temperature (25-30° C.). The suitable period of time may be about 5-7 hours. The reaction mixture may be extracted with suitable solvent. The suitable solvent may be ethyl acetate. The organic layer may be dried and evaporated to dryness to obtain a product. The product obtained may be taken in a non-polar solvent. The non-polar solvent may be any hydrocarbon solvent. Preferably the solvent is cyclohexane. The product may be filtered and dried to obtain compound of formula (V). Optionally the product may be further washed with another solvent such as pentane to obtain the desired purity.

In another embodiment, there is provided process for preparation of compound of formula (II) or salt thereof, which process comprising the step of reacting 2-chloro benzoic acid with a compound (VII)

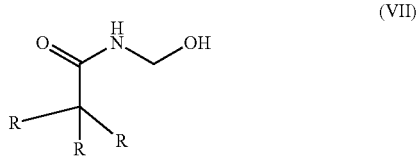

(VII)

to obtain compound of formula (VI a)

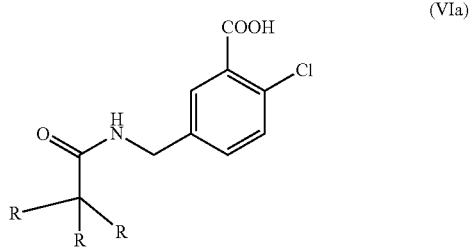

(VIa)

wherein R is chloro, bromo, or methyl.

In this embodiment, compound (VII) can be selected from 2,2,2-Trichloro-N-(hydroxymethyl)acetamide, 2,2,2-Tribromo-N-(hydroxymethyl) acetamide or 2,2,2-Trimethyl-N-(hydroxymethyl)acetamide. In a further embodiment the reaction may be carried out in presence of an acid. The acid may be inorganic or organic acid. Preferably, the acid may be inorganic acid. More preferably, the acid is sulphuric acid ($H_2SO_4$). The reaction may be carried out at a suitable temperature. The suitable temperature may be room temperature (25-30° C.).

After the completion of the reaction, the reaction mass may be poured in cold water to obtain a compound represent by formula (VI a), which may be filtered and dried. The compound of formula (VI a) may be further purified by taking the compound in a suitable solvent or mixture thereof and optionally heating the mixture till a clear solution is obtained. The suitable solvent may include, but not limited to, hydrocarbon solvents such as toluene, xylene, n-heptane, cyclohexane and n-hexane. Preferably, the suitable solvent is toluene and/or methyl ethyl ketone. The clear solution may be cooled to obtain the compound of formula (VI a) which may be filtered and dried. The purification step may be further repeated to obtain the desired purity.

Pharmaceutical Compositions

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical composition may also include one or more pharmaceutically acceptable auxiliary agents, wetting agents, suspending agents, preserving agents, buffers, sweetening agents, flavoring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques, e.g., as described in *Remington: The Science and Practice of Pharmacy*, 20$^{th}$ Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

DEFINITIONS

The term "crystalline" as used herein, means having a regularly repeating arrangement of molecules or external face planes.

The term "amorphous" as used herein, means essentially without regularly repeating arrangement of molecules or external face planes.

Unless stated otherwise, percentages stated throughout this specification are weight/weight (w/w) percentages.

The term "mixture" as used herein, means a combination of at least two substances, in which one substance may be completely miscible, partially miscible or essentially immiscible in the other substance.

The term "treating" or "treatment" of a state, disorder or condition includes; (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

All powder X-ray diffraction patterns were obtained using: Panlytical X'PERT-PRO diffractometer model and measured with Cu—Kα1 radiation at wavelength of 1.54060 A°. The obtained powder X-ray diffraction profiles were integrated using X'Pert High Score Plus Software.

It is meant to be understood that peak heights in a powder x-ray diffraction pattern may vary and will be dependent on variables such as the temperature, crystal size, crystal habit, sample preparation or sample height in the analysis well of the Scintag×2 Diffraction Pattern System.

All FTIR spectra were recorded using KBr on Perkin-Elmer instrument (Model: Spectrum One). The data was processed using Spectrum One Software.

As used herein, the term "average particle size" (or synonymously, "mean particle size") refers to the distribution of particles, wherein about 50 volume percent of all the particles measured have a size less than the defined average particle size value and about 50 volume percent of all measurable particles measured have a particle size greater than the defined average particle size value. This can be identified by the term "$D_{50}$" or "d (0.5)".

The term "$D_{10}$" refers to the distribution of particles, wherein about 10 volume percent of all the particles measured have a size less than the defined particle size value. This can be identified by the term "d(0.1)" as well. Similarly, as used herein, the term "$D_{90}$" refers to the distribution of particles, wherein about 90 volume percent of all the particles measured have a size less than the defined particle size value. This can be identified by the term or "d (0.9)" as well.

The average particle size can be measured using various techniques like laser diffraction, photon correlation spectroscopy and Coulter's principle. Typically, instruments like ZETASIZER® 3000 HS (Malvern® Instruments Ltd., Malvern, United Kingdom), NICOMP 388™ ZLS system (PSS-Nicomp Particle Sizing Systems, Santa Barbara, Calif., USA), or Coulter Counter are generally used to determine the mean particle size. Preferably, Mastersizer 2000 (Malvern® Instruments Ltd., Malvern, United Kingdom) is used to determine the particle size of the particles.

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-d$_6$: Hexadeuterodimethyl sulfoxide; AcOEt: ethyl acetate; equiv. or eq.: equivalents; h: hour(s); L: liters; CDCl$_3$: deuterated chloroform; CHCl$_3$: chloroform; EtOAc or EA: ethyl acetate; DCM or MDC: dichloromethane or methylene dichloride; DMSO: dimethyl sulfoxide; DMF: N,N-dimethylformamide; MTBE: Methyl tert-butyl ether; DSC: Differential scanning calorimetry; K$_2$CO$_3$: potassium carbonate; MeOH: methanol; EtOH: ethanol; NaHCO$_3$: sodium bicarbonate; Na₂CO₃: sodium carbonate; THF: tetrahydrofuran; J: Coupling constant in units of Hz; RT or rt: room temperature (22-30° C.); q.s.: quantity sufficient; aq.: aqueous; equiv. or eq.: equivalents; conc.: concentrated; min: minutes; i.e.: that is; h or hrs: hours.

The parameters mentioned in the description which characterize the polymorphic nature, particle size by the measuring techniques and methods are described below:

Particle Size Distribution Studies:

The particle size distribution was measured using Mastersizer 2000 (Malvern® instruments Ltd., Malvern, United Kingdom) with following measuring equipment and settings:

Instrument: Malvern Mastersizer 2000
Sample Handling Unit: Hydro 2000S (A)
Dispersant RI: 1.33
Dispersant: Water
Sample quantity: 25-50 mg
Measurement time: 5.0 sec Powder X-Ray Diffraction Studies:

All powder X-ray diffraction patterns were obtained using: Panlytical X'PERT-PRO diffractometer model and measured with Cu-Kα1 radiation at wavelength of 1.54060 A°. The obtained powder X-ray diffraction profiles were integrated using X'Pert High Score Plus Software.

Fourier Transform Infrared Spectroscopy (FT-IR) Studies

About 200 mg of KBr, previously dried at 200° C. and cooled, was taken into a mortar and grinded to a fine powder. 2-3 mg of test sample was added to it and was mixed well and grinded to obtain a uniform sample. A small quantity of the sample powder was taken, put it between dies and compressed it by applying 10-15 pound pressure to obtain a semitransparent pellet. The IR spectrum of the pellet was recorded from 4000 cm$^{-1}$ to 450 cm$^{-1}$ taking air as a reference.

HPLC Conditions:

Apparatus: A High Performance Liquid Chromatograph equipped with quaternary gradient pumps, variable wavelength UV detector attached with data recorder and Integrator software or equivalent.

Column: Zorbax Eclipse XDB C-8, 150 mm×4.6 mm, 5 t or equivalent

Mobile phase: A: Buffer B: Methanol (Gradient Program)

Buffer: Water, pH adjusted to 2.2 with trifluoroacetic acid solution. Filter through 0.45µ filter paper and degas.

Diluent: Water: Methanol (20:80 v/v)
Flow Rate: 1.0 mL/minute
Detection wavelength: UV 270 nm
Column temperature: 25° C.
Injection volume: 20 µl
Run time: 60 min Test Solution:

25 mg of the compound was weighed and transferred into a 50 mL volumetric flask. Methanol (5 ml) was added and it was sonicated to dissolve. The diluent was added to make up the solution to the mark of the flask.

Procedure:

The equal volumes of blank (diluent) and test solution were separately injected into the High Performance liquid chromatography. The responses were recorded eliminating the peaks due to blank and the chromatographic purity by area was calculated by normalization method.

The following examples are presented to provide what is believed to be the most useful and readily understood description of procedures and conceptual aspects of this invention. The examples provided below are merely illustrative of the invention and are not intended to limit the same to disclosed embodiments. Variations and changes obvious to one skilled in the art are intended to be within the scope and nature of the invention.

Intermediate 1

Preparation of 2-chloro-5-((2,2,2-trifluoroacetamido)methyl)benzoic acid

To a solution of 2-chlorobenzoic acid (930.0 gm, 5.96 mol) in conc. sulphuric acid (5580 ml), 2,2,2-trifluoro-N-(hydroxymethyl)acetamide (930.0 gm, 6.0 mol) was added at 20° C. and the reaction mixture was stirred for 15.0 h at 25-30° C. After the completion of the reaction, the reaction was slowly quenched with cold water (37.0 lit) at 10-15° C. The precipitated product was filtered and dried. The obtained product was purified using mixture of toluene and methylethylketone (7:1×4 times) to obtain 580.0 gm of the tittle compound having chemical purity of 98.0%, determined by HPLC.

Intermediate 2

Preparation of 2-chloro-5-((2,2,2-trifluoroacetamido)methyl)benzamide

To a solution of 2-chloro-5-((2,2,2-trifluoroacetamido)methyl)benzoic acid (575.0 gm, 2.04 mol) in THF (3450.0 ml) catalytic amount of DMF (2.9 ml) was added. Oxalyl chloride (389.0 gm, 3.06 mol) was added to the reaction mixture slowly at 20° C. The reaction mixture was stirred for 2.0 h at 25-30° C. After the completion of the reaction, the reaction mass was distilled under reduced pressure to obtain the acid chloride derivative. THF (3450.0 ml) was added and the reaction mixture was cooled to 0-5° C. Ammonia gas was purged to the reaction mixture till a pH of 7-9 was obtained and the reaction mixture was stirred for 1.0 h at 20-25° C. After the completion of the reaction, the reaction was quenched with water (7.0 lit). The reaction mass was extracted with ethyl acetate (2×7.0 lit). The organic layer was washed with brine. The organic layer was concentrated under reduced pressure. Cyclohexane (1440 ml) was charged to the residue and the mixture was maintained for 1.0 h at 25-30° C. The product precipitated was filtered and dried to obtain 505.0 gm of the title compound having chemical purity of 95.0%, determined by HPLC.

Intermediate 3

Preparation of tert-butyl 2-(4-(trifluoromethyl)phenyl)hydrazinecarboxylate

To a solution of 4-(trifluoromethyl)phenyl]hydrazine HCl (400.0 gm, 1.88 mol) in THF (2400 ml), water (1200 ml) was added. Sodium carbonate (480 gm, 4.52 mol) was added to the reaction mixture slowly. The reaction mass was cooled to 10-15° C. and di-tert-butyl dicarbonate (596 gm, 2.73 mol) was added slowly. The reaction mixture was stirred for 6.0 h at 25-30° C. After the completion of the reaction, the reaction was quenched with water (15.0 lit) and the reaction mass was extracted with ethyl acetate (2×5.0 lit). The organic layer was washed with water followed by brine. The organic layer was concentrated under reduced pressure. Cyclohexane (1.0 lit) was charged to the obtained residue and it was stirred for 1.0 h at 25-30° C. The precipitated product was filtered and dried to obtain 480.0 gm of the title compound having chemical purity of 99%, determined by HPLC.

Intermediate 4

Preparation of N-(4-chloro-3-(5-oxo-1-(4-(trifluoromethyl)phenyl)-4,5-dihydro-1H-1,2,4-triazol-3-yl) benzyl)-2,2,2-trifluoroacetamide A solution of 2-chloro-5-((2,2,2-trifluoroacetamido) methyl)benzamide (500 gm, 1.78 mol) in MDC (5.0 lit) was cooled to 20° C. and oxalyl chloride (295 gm, 2.32 mol) was added to it slowly. The reaction mixture was stirred at 45-50° C. for 4.0 h. The reaction mass was concentrated under reduced pressure. A solution of tert-butyl 2-[4-(trifluoromethyl)phenyl]hydrazinecarboxylate (492 gm, 1.78 mmol) in MDC (6.0 lit) was prepared separately and was added to the above residue at 15-20° C. The reaction mixture was stirred for 4.0 h. Trifluoroacetic acid (600.0 ml) was added to the reaction mixture at 10-15° C. and the reaction was stirred for 15.0 h at 25-30° C. After the completion of the reaction, cyclohexane (12.0 lit) was added to the reaction mixture and it was maintained for 1.0 h at 25-30° C. The product precipitated was filtered and dried to obtain 734.0 gm of the title compound having chemical purity of 98%, determined by HPLC.

Example 1

Preparation of N-(4-chloro-3-(5-oxo-1-(4-(trifluoromethyl)phenyl)-4,5-dihydro-1H-1,2,4-triazol-3-yl) benzyl)pivalamide To a solution of N-(4-chloro-3-(5-oxo-1-(4-(trifluoromethyl)phenyl)-4,5-dihydro-1H-1,2,4-triazol-3-yl)benzyl)-2,2,2-trifluoroacetamide (35.0 gm, 0.075 mol) in THF (175.0 ml) water (280.0 ml) was added and the reaction mixture was cooled to 5° C. Sodium hydroxide solution (10.55 gm, 0.263 mol) in water (70.0 ml) was added slowly to the reaction mixture and it was stirred for 1.0 h at 15-20° C. The reaction mixture was cooled to 5° C. and pivaloyl chloride (13.6 gm, 0.113 mol) was added slowly. The reaction mixture was stirred for 30.0 min at same temperature. The pH of the reaction mixture was adjusted to about 6-7 by adding 20% HCl or 20.0% sodium hydroxide solution and the reaction mixture was maintained for another 30.0 min at 10-15° C. The product precipitated was filtered and dried to obtain 29.0 gm of the title compound having chemical purity of 99.5%, determined by HPLC.

Example 2

Preparation of Form (I) of N-(4-chloro-3-(5-oxo-1-(4-(trifluoromethyl)phenyl)-4,5-dihydro-1H-1,2,4-triazol-3-yl)benzyl)pivalamide Method 1:
N-(4-chloro-3-(5-oxo-1-(4-(trifluoromethyl)phenyl)-4,5-dihydro-1H-1,2,4-triazol-3-yl)benzyl)pivalamide (29.0 gm) was dissolved in 15% methanol in ethyl acetate (1450 ml) at 45° C. and the reaction mixture was concentrated under reduced pressure. To the residue obtained, 10.0% methanol in MTBE (290.0 ml) was charged and the mixture was stirred for 1.0 h at 25-30° C. The mixture was filtered and the filtrate was dried to obtain 25.0 gm of Form (I) of N-(4-chloro-3-{5-oxo-1-[4-(trifluoromethyl)phenyl]-4,5-dihydro-1H-1,2,4-triazol-3-yl} benzyl)-pivalamide.

Method 2:
N-(4-chloro-3-(5-oxo-1-(4-(trifluoromethyl)phenyl)-4,5-dihydro-1H-1,2,4-triazol-3-yl) benzyl)pivalamide (10.0 gm) was taken in a mixture of diethyl ether (60 ml) and methanol (30 ml) and the reaction mixture was stirred for 2 h. The mixture was filtered and the solid was dried to obtain 7.5 gm of Form (I) of N-(4-chloro-3-{5-oxo-1-[4-(trifluoromethyl) phenyl]-4,5-dihydro-1H-1,2,4-triazol-3-yl}benzyl)-pivalamide.

Example 3

Preparation of Form (II) of N-(4-chloro-3-(5-oxo-1-(4-(trifluoromethyl)phenyl)-4,5-dihydro-1H-1,2,4-triazol-3-yl)benzyl)pivalamide Method 1:
N-(4-chloro-3-(5-oxo-1-(4-(trifluoromethyl)phenyl)-4,5-dihydro-1H-1,2,4-triazol-3-yl) benzyl)pivalamide (1.0 gm) was heated to melt by external heating. The mass was cooled to room temperature (25-30° C.) slowly to obtain 0.90 gm of Form (II) of N-(4-chloro-3-{5-oxo-1-[4-(trifluoromethyl) phenyl]-4,5-dihydro-1H-1,2,4-triazol-3-yl}benzyl)-pivalamide.

Method 2:
N-(4-chloro-3-(5-oxo-1-(4-(trifluoromethyl)phenyl)-4,5-dihydro-1H-1,2,4-triazol-3-yl) benzyl)pivalamide (1.0 gm) was crystallized in ethyl acetate (5 ml) and methanol (5 ml) to obtain 0.60 gm of Form (II) of N-(4-chloro-3-{5-oxo-1-[4-(trifluoromethyl)phenyl]-4,5-dihydro-1H-1,2,4-triazol-3-yl}benzyl)-pivalamide.

Method 3:
N-(4-chloro-3-(5-oxo-1-(4-(trifluoromethyl)phenyl)-4,5-dihydro-1H-1,2,4-triazol-3-yl) benzyl)pivalamide (1.0 gm) was slurred in ethyl acetate (3 ml) to obtain 0.75 gm of Form (II) of N-(4-chloro-3-{5-oxo-1-[4-(trifluoromethyl)phenyl]-4,5-dihydro-1H-1,2,4-triazol-3-yl}benzyl)-pivalamide Example 4

Preparation of Form (III) of N-(4-chloro-3-(5-oxo-1-(4-(trifluoromethyl)phenyl)-4,5-dihydro-1H-1,2,4-triazol-3-yl)benzyl)pivalamide N-(4-chloro-3-(5-oxo-1-(4-(trifluoromethyl)phenyl)-4,5-dihydro-1H-1,2,4-triazol-3-yl) benzyl)pivalamide (10.0 gm) was taken in THF (150 ml). The mixture was stirred for 10-15 min at 25-30° C. to obtain clear solution. n-Heptane (500 ml) was added to the clear solution at a moderate speed in 5-10 min. A solid was precipitated which was further stirred for 3-4 h. The mixture was filtered, the solid was washed with n-heptane (50 ml) and it was dried to obtain 8.3 gm of Form (III) of N-(4-chloro-3-{5-oxo-1-[4-(trifluoromethyl)phenyl]-4,5-dihydro-1H-1,2,4-triazol-3-yl}benzyl)-pivalamide.

Example 5

Preparation of amorphous form of N-(4-chloro-3-(5-oxo-1-(4-(trifluoromethyl)phenyl)-4,5-dihydro-1H-1,2,4-triazol-3-yl)benzyl)pivalamide N-(4-chloro-3-(5-oxo-1-(4-(trifluoromethyl)phenyl)-4,5-dihydro-1H-1,2,4-triazol-3-yl) benzyl)pivalamide (1.0 gm) was heated to melt by external heating. The mass was cooled to room temperature (25-30° C.) rapidly to obtain 0.80 gm of amorphous form of N-(4-chloro-3-{5-oxo-1-[4-(trifluoromethyl)phenyl]-4,5-dihydro-1H-1,2,4-triazol-3-yl}benzyl)-pivalamide (>95%).

Example 6

Stability studies of compound of formula II: (N-(4-chloro-3-(5-oxo-1-(4-(trifluoromethyl) phenyl)-4,5-dihydro-1H-1,2,4-triazol-3-yl)benzyl)pivalamide)

The compound of formula II was stored under conditions as shown in below table and a total amount of degradation products (related substances) as well as single maximum impurity formed during storage was estimated by HPLC. The material was packed in inner clear polythene bag under nitrogen lined with black polythene bag, covered with triple laminated aluminium bag placed in HDPE drum and subjected to the conditions mentioned in the table 5.

TABLE 5

| Storage conditions | Condition 1 | Condition 2 |
| --- | --- | --- |
| Temperature | 25 ± 2° C. | 40 ± 2° C. |
| Humidity (% RH) | 60 ± 5% RH | 75 ± 5% RH |
| Testing intervals | 0, 1, 2, 3, 6 months | 0, 1, 2, 3, 6 months |

The result of stability studies of compound of formula (II) carried out under the conditions mentioned in the table 5 is presented in tables 6 and 7.
Stability of Compound of Formula II Under the Storage Condition 1:

TABLE 6

| | Storage period (months) | | | | |
| --- | --- | --- | --- | --- | --- |
| Test Item (%) | 0 | 1 | 2 | 3 | 6 |
| Related substances | 0.13 | NT | NT | 0.14 | 0.14 |
| Single max. impurity | 0.13 | NT | NT | 0.14 | 0.14 |

NT: not tested

Stability of Compound of Formula II Under the Storage Condition 2:

TABLE 7

| | Storage period (months) | | | | |
| --- | --- | --- | --- | --- | --- |
| Test Item (%) | 0 | 1 | 2 | 3 | 6 |
| Related substances | 0.13 | 0.14 | 0.13 | 0.14 | 0.13 |
| Single max. impurity | 0.13 | 0.14 | 0.13 | 0.14 | 0.13 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:

1. A crystalline form of N-(4-chloro-3-(5-oxo-1-(4-(trifluoromethyl)phenyl)-4,5-dihydro-1H-1,2,4-triazol-3-yl)benzyl)pivalamide (Compound formula II), structurally represented as

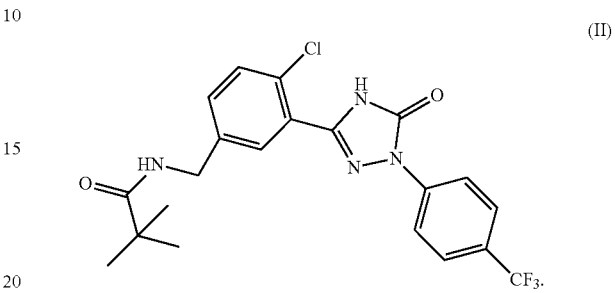

2. The crystalline form according to claim 1, having a characteristic X-ray diffraction pattern comprising of the peaks expressed in terms of 2θ±0.2: 5.66, 6.55 and 13.05.

3. The crystalline form according to claim 1, having a characteristic X-ray diffraction pattern comprising of the peaks expressed in terms of 2θ±0.2: 5.66, 6.55, 12.51, 13.05, 15.01, 16.59 and 25.69.

4. The crystalline form according to claim 1, having a characteristic X-ray diffraction pattern comprising of the following peaks expressed in terms of 2θ±0.2: 24.57 and 30.85.

5. The crystalline form according to claim 1, having a characteristic X-ray diffraction pattern comprising of the following peaks expressed in terms of 2θ±0.2: 7.02, 12.54, 16.64, 18.31, 24.57, 25.74 and 30.85.

6. The crystalline form according to claim 1, having a characteristic X-ray diffraction pattern comprising of the following peaks expressed in terms of 2θ±0.2: 13.92, 31.01, 35.13 and 38.54.

7. The crystalline form according to claim 1, having a characteristic X-ray diffraction pattern comprising of the following peaks expressed in terms of 2θ±0.2: 7.00, 12.60, 13.92, 16.71, 20.89, 24.55, 31.01, 35.13 and 38.54.

8. The crystalline compound of formula (II) according to claim 1, having an average particle size value ($D_{50}$) in the range from about 1 μm to about 100 μm.

9. An amorphous form of N-(4-chloro-3-(5-oxo-1-(4-(trifluoromethyl)phenyl)-4,5-dihydro-1H-1,2,4-triazol-3-yl) benzyl) pivalamide.

10. A process for preparation of crystalline form of N-(4-chloro-3-(5-oxo-1-(4-(trifluoromethyl)phenyl)-4,5-dihydro-1H-1,2,4-triazol-3-yl)benzyl)pivalamide, having a characteristic X-ray diffraction pattern comprising of the peaks expressed in terms of 2θ±0.2: 5.66, 6.55, and 13.05, which process comprises the following steps:
    a) taking N-(4-chloro-3-(5-oxo-1-(4-(trifluoromethyl) phenyl)-4,5-dihydro-1H-1,2,4-triazol-3-yl)benzyl) pivalamide in a mixture of diethyl ether and methanol or in a mixture of methyl tert-butyl ether and methanol;
    b) stirring the mixture of step (a); and
    c) isolating the desired compound.

* * * * *